United States Patent
Lito

(10) Patent No.: US 11,590,133 B2
(45) Date of Patent: Feb. 28, 2023

(54) METHODS AND COMPOSITIONS FOR TREATMENT OF BRAF MUTANT CANCERS

(71) Applicant: MEMORIAL SLOAN KETTERING CANCER CENTER, New York, NY (US)

(72) Inventor: Piro Lito, New York, NY (US)

( * ) Notice: Subject to any disclaimer, the term of this patent is extended or adjusted under 35 U.S.C. 154(b) by 241 days.

(21) Appl. No.: 16/468,072

(22) PCT Filed: Dec. 11, 2017

(86) PCT No.: PCT/US2017/065532
§ 371 (c)(1),
(2) Date: Jun. 10, 2019

(87) PCT Pub. No.: WO2018/107146
PCT Pub. Date: Jun. 14, 2018

(65) Prior Publication Data
US 2020/0009138 A1    Jan. 9, 2020

Related U.S. Application Data

(60) Provisional application No. 62/432,608, filed on Dec. 11, 2016.

(51) Int. Cl.
| | |
|---|---|
| *A61K 31/506* | (2006.01) |
| *A61K 31/404* | (2006.01) |
| *A61K 31/437* | (2006.01) |
| *A61K 31/4439* | (2006.01) |
| *A61K 31/454* | (2006.01) |
| *A61K 31/496* | (2006.01) |
| *A61K 31/5025* | (2006.01) |
| *A61K 31/517* | (2006.01) |
| *A61K 31/519* | (2006.01) |
| *A61K 45/06* | (2006.01) |
| *A61K 31/5513* | (2006.01) |

(52) U.S. Cl.
CPC .......... *A61K 31/506* (2013.01); *A61K 31/404* (2013.01); *A61K 31/437* (2013.01); *A61K 31/4439* (2013.01); *A61K 31/454* (2013.01); *A61K 31/496* (2013.01); *A61K 31/5025* (2013.01); *A61K 31/517* (2013.01); *A61K 31/519* (2013.01); *A61K 31/5513* (2013.01); *A61K 45/06* (2013.01)

(58) Field of Classification Search
CPC .. A61K 31/437; A61K 31/444; A61K 31/506; A61K 31/519; A61K 31/06; A61K 31/404; A61K 31/4439; A61K 31/454; A61K 31/496; A61K 31/5025; A61K 31/517; A61K 31/5513; A61K 31/65; A61K 45/06; A61P 35/00
See application file for complete search history.

(56) References Cited

U.S. PATENT DOCUMENTS

| | | |
|---|---|---|
| 2004/0147428 A1 | 7/2004 | Pluenneke |
| 2007/0020657 A1* | 1/2007 | Grebe ................ C12Q 1/6886 435/6.16 |
| 2009/0105329 A1 | 4/2009 | Chiao et al. |
| 2016/0008332 A1 | 1/2016 | Haq et al. |
| 2016/0106835 A1 | 4/2016 | Hoos et al. |

FOREIGN PATENT DOCUMENTS

| | | | |
|---|---|---|---|
| WO | 2009018238 A1 | 2/2009 | |
| WO | WO-2013070996 A1 * | 5/2013 | ........... A61K 31/506 |
| WO | WO-2015156674 A2 * | 10/2015 | ........... A61K 31/519 |
| WO | 2016130917 A1 | 8/2016 | |

OTHER PUBLICATIONS

Garcia et. al., Clin. Cancer Res., vol. 18(17), pp. 4806-4819, publ. 2012 (Year: 2012).*
Chapman, P. B et al. Improved survival with vemurafenib in melanoma with BRAFV600E mutation. The New England Journal of medicine 364, 2507-2516, doi:10.1056/NEJMoa1103782 (2011).
Flaherty, K. T. et al. Inhibition of mutated, activated BRAF in metastatic melanoma. The New England journal of medicine 363, 809-819, doi:10.1056/NEJMoa1002011 (2010).
Planchard, D. et al. Dabrafenib in patients with BRAF(V600E)-positive advanced non-small-cell lung cancer: a single-arm, multicentre, open-label, phase 2 trial. The Lancet. Oncology 17, 642-650, doi:10.1016/S1470-2045(16)00077-2 (2016).
Hyman, D. M. et al. Vemurafenib in Multiple Nonmelanoma Cancers with BRAF V600 Mutations. The New England journal of medicine 373, 726-736, doi:10.1056/NEJMoa1502309 (2015).
Flaherty, K. T. et al. Combined BRAF and MEK inhibition in melanoma with BRAF V600 mutations. The New England journal of medicine 367, 1694-1703, doi:10.1056/NEJMoa1210093 (2012).
Larkin, J. et al. Combined vemurafenib and cobimetinib in BRAF-mutated melanoma. The New England journal of medicine 371, 1867-1876, doi:10.1056/NEJMoa1408868 (2014).
Long, G. V. et al. Combined BRAF and MEK inhibition versus BRAF inhibition alone in melanoma. The New England journal of medicine 371, 1877-1888, doi:10.1056/NEJMoa1406037 (2014).
Robert, C. et al. Improved overall survival in melanoma with combined dabrafenib and trametinib. The New England journal of medicine 372, 30-39, doi:10.1056/NEJMoa1412690 (2015).
Planchard, D. et al. Dabrafenib plus trametinib in patients with previously treated BRAF(V600E)-mutant metastatic non-small cell lung cancer: an open-label, multicentre phase 2 trial. The Lancet. Oncology 17, 984-993, doi:10.1016/S1470-2045(16)30146-2 (2016).
Bollag, G. et al. Clinical efficacy of a RAF inhibitor needs broad target blockade in BRAF-mutant melanoma. Nature 467, 596-599, doi:10.1038/nature09454 (2010).

(Continued)

*Primary Examiner* — Sarah Pihonak
(74) *Attorney, Agent, or Firm* — Grimes & Yvon LLP

(57) ABSTRACT

The present invention provides various compositions and methods useful for the treatment of BRAF-mutant tumors, such as $BRAF^{V600E}$-mutant tumors. In some embodiments such methods involve administration of three active agents—a RAF inhibitor, a MEK inhibitor, and an ERK inhibitor. The present invention also provides novel intermittent dosing regimens for these three active agents that maintain maximal anti-tumor efficacy while also minimizing toxicity.

18 Claims, 8 Drawing Sheets

(56) References Cited

OTHER PUBLICATIONS

Wong, D. J. et al. Antitumor activity of the ERK inhibitor SCH772984 [corrected] against BRAF mutant, NRAS mutant and wild-type melanoma. Molecular cancer 13, 194, doi:10.1186/1476-4598-13-194 (2014).

Das Thakur, M. et al. Modelling vemurafenib resistance in melanoma reveals a strategy to forestall drug resistance. Nature 494, 251-255, doi:10.1038/nature11814 (2013).

Shi, H. et al. Acquired resistance and clonal evolution in melanoma during BRAF inhibitor therapy. Cancer discovery 4, 80-93, doi:10.1158/2159-8290.CD-13-0642 (2014).

Shi, H. et al. Melanoma whole-exome sequencing identifies (V600E)B-RAF amplification-mediated acquired B-RAF inhibitor resistance. Nature communications 3, 724, doi:10.1038/ncomms1727 (2012).

Jha, S. et al. Dissecting Therapeutic Resistance to ERK Inhibition. Molecular cancer therapeutics 15, 548-559, doi:10.1158/1535-7163.MCT-15-0172 (2016).

Yao, Z. et al. BRAF Mutants Evade ERK-Dependent Feedback by Different Mechanisms that Determine Their Sensitivity to Pharmacologic Inhibition. Cancer cell 28, 370-383, doi:10.1016/j.ccell.2015.08.001 (2015).

Joseph, E. W. et al. The RAF inhibitor PLX4032 inhibits ERK signaling and tumor cell proliferation in a V600E BRAF-selective manner. Proceedings of the National Academy of Sciences of the United States of America 107, 14903-14908, doi:10.1073/pnas.1008990107 (2010).

Kim, K. B. et al. Phase II study of the MEK1/MEK2 inhibitor Trametinib in patients with metastatic BRAF-mutant cutaneous melanoma previously treated with or without a BRAF inhibitor. Journal of clinical oncology: official journal of the American Society of Clinical Oncology 31, 482-489, doi:10.1200/JCO.2012.43.5966 (2013).

Holderfield, M., Deuker, M. M., McCormick, F. & McMahon, M. Targeting RAF kinases for cancer therapy: BRAF-mutated melanoma and beyond. Nature reviews. Cancer 14, 455-467, doi:10.1038/nrc3760 (2014).

Heidorn, S. J. et al. Kinase-dead BRAF and oncogenic RAS cooperate to drive tumor progression through CRAF. Cell 140, 209-221, doi:10.1016/j.cell.2009.12.040 (2010).

Poulikakos, P. I., Zhang, C., Bollag, G., Shokat, K. M. & Rosen, N. RAF inhibitors transactivate RAF dimers and ERK signalling in cells with wild-type BRAF. Nature 464, 427-430, doi:10.1038/nature08902 (2010).

Corcoran, R. B. et al. EGFR-mediated re-activation of MAPK signaling contributes to insensitivity of BRAF mutant colorectal cancers to RAF inhibition with vemurafenib. Cancer discovery 2, 227-235, doi:10.1158/2159-8290.CD-11-0341 (2012).

Prahallad, A. et al. Unresponsiveness of colon cancer to BRAF(V600E) inhibition through feedback activation of EGFR. Nature 483, 100-103, doi:10.1038/nature10868 (2012).

Shi, H. et al. A novel AKT1 mutant amplifies an adaptive melanoma response to BRAF inhibition. Cancer discovery 4, 69-79, doi:10.1158/2159-8290.CD-13-0279 (2014).

Sun, C. et al. Reversible and adaptive resistance to BRAF(V600E) inhibition in melanoma. Nature 508, 118-122, doi:10.1038/nature13121 (2014).

Maertens, O. et al. Elucidating distinct roles for NF1 in melanomagenesis. Cancer discovery 3, 338-349, doi:10.1158/2159-8290.CD-12-0313 (2013).

Johannessen, C. M. et al. A melanocyte lineage program confers resistance to MAP kinase pathway inhibition. Nature 504, 138-142, doi:10.1038/nature12688(2013).

Zhang, C. et al. RAF inhibitors that evade paradoxical MAPK pathway activation. Nature 526, 583-586, doi:10.1038/nature14982 (2015).

Cancer Genome Atlas Research Network "Comprehensive molecular profiling of lung adenocarcinoma", Jul. 31, 2014, vol. 511, Nature, pp. 543-550.

Carlino et al. "Differential Activity of MEK and ERK Inhibitors in BRAF Inhibitor Resistant Melanoma" Molecular Oncology, May 1, 2014 (May 1, 2014), vol. 8, No. 3, pp. 544-554.

Chung et al. "Hematopoietic Stem Cell Origin of BRAFV600E Mutations in Hairy Cell Leukemia" Sci Transl Med. May 28, 2014; 6(238): 238ra71. doi:10.1126/scitranslmed.3008004.

Firestone & Settleman "A three-drug combination to treat BRAF-mutant cancers", Nature Medicine vol. 23, No. 8, Aug. 2017, pp. 913-914.

Krepler et al. "Targeting Notch Enhances the Efficacy of ERK Inhibitors in BRAF-V600E Melanoma," Oncotarget, Sep. 16, 2016 (Sep. 16, 2016), vol. 7, No. 44. pp. 71211-71222.

Lito et al. "Relief of Profound Feedback Inhibition of Mitogenic Signaling by RAF Inhibitors Attenuates Their Activity in BRAFV600E Melanomas," Cancer Cell, Nov. 13, 2012 (Nov. 13, 2012), vol. 22, pp. 668-682.

Lito et al. "Tumor Adaptation and Resistance to RAF Inhibitors," Nature Medicine, Nov. 7, 2013 (Nov. 7, 2013), vol. 19, pp. 1401-1409. entire document.

Lito et al. "Allele-specific inhibitors inactivate mutant KRAS G12C by a trapping mechanism" Science. Feb. 5, 2016; 351(6273): 604-608.

Lito et al. Disruption of CRAF-mediated MEK activation is required for effective MEK inhibition in KRAS mutant tumors, Cancer Cell. May 12, 2014; 25(5): 697-710.

Morris et al. "Discovery of a Novel ERK Inhibitor with Activity in Models of Acquired Resistance to BRAF and MEK inhibitors," Cancer Discovery, Jul. 1, 2013 (Jul. 1, 2013), vol. 3, pp. 742-750.

Xue & Lito "Predicting MEK Inhibitor Response in Lung Cancer: A Proper Signature Is Required", Clin Cancer Res; 23(6) Dec. 6, 2016.

Xue et al. "An Approach to Suppress the Evolution of Resistance in BRAF V600E-Mutant Cancer," Nature Medicine, Jul. 17, 2017 (Jul. 17, 2017), vol. 23, No. 8, pp. 929-937.

International Search Report & Written Opinion for PCT/US2017/065532, dated Apr. 6, 2018.

* cited by examiner

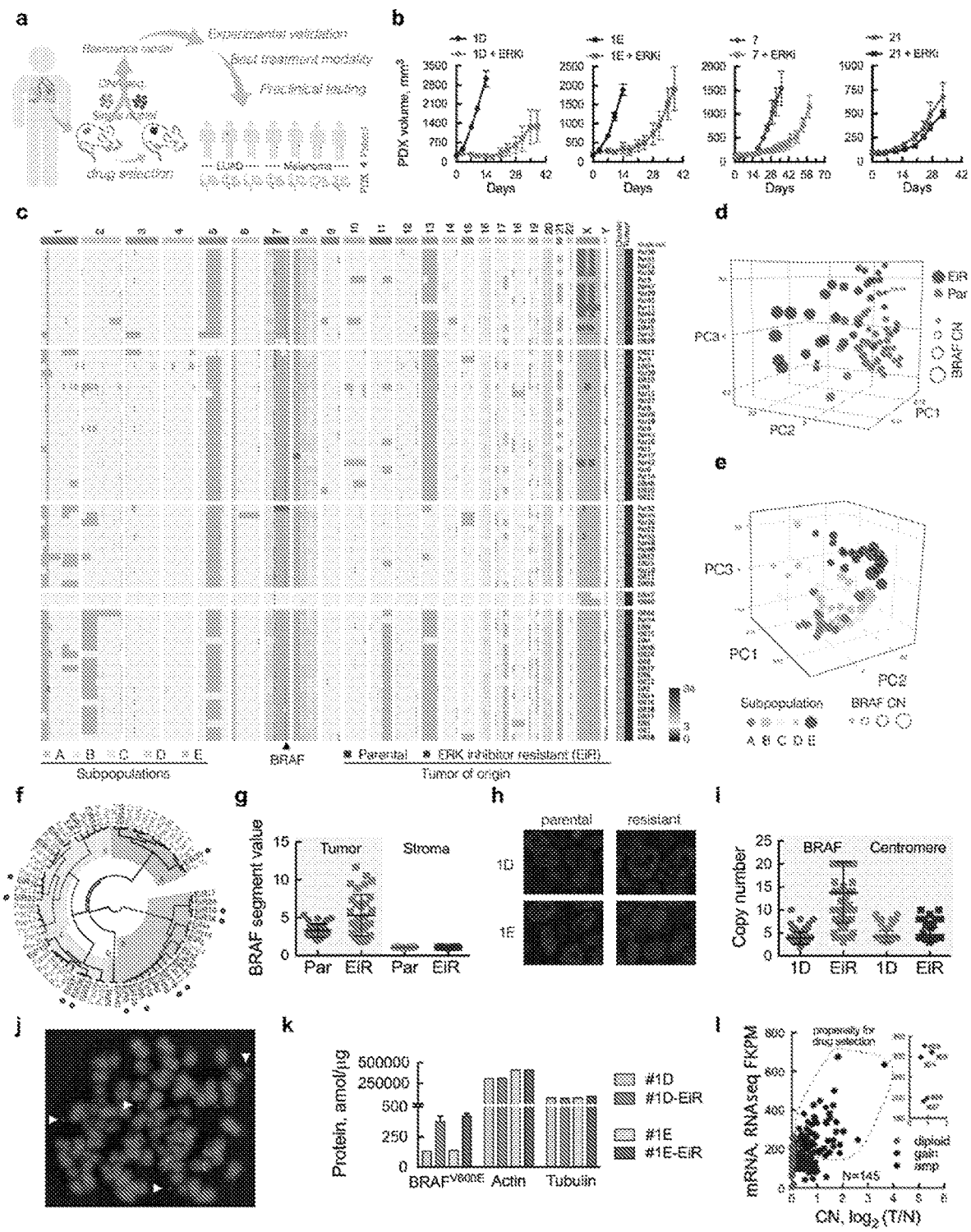
Fig. 1A-I

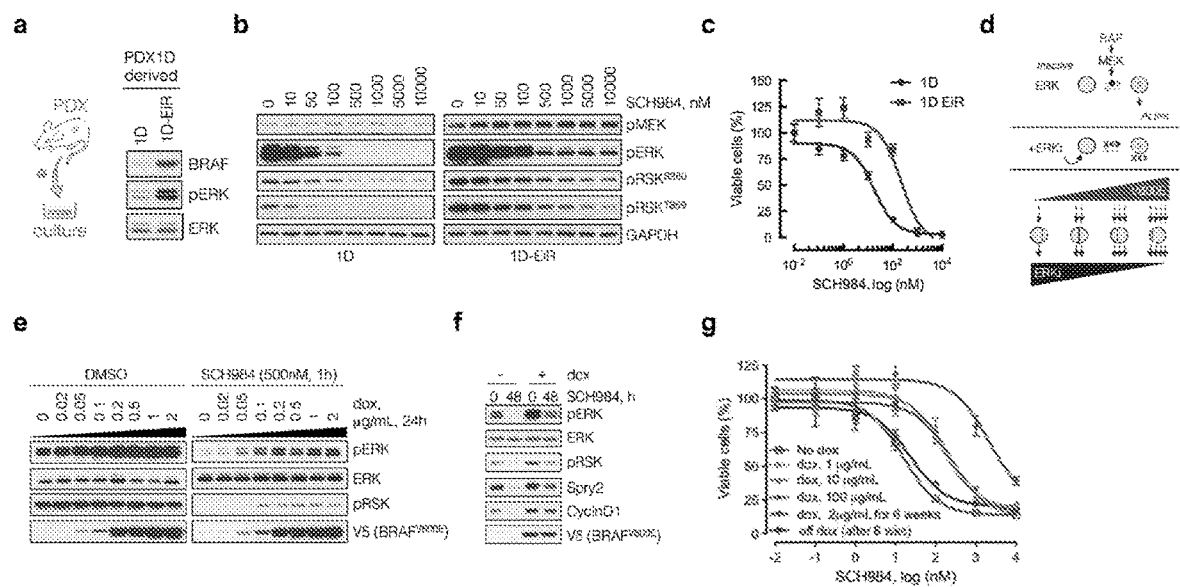
Fig. 2A-G

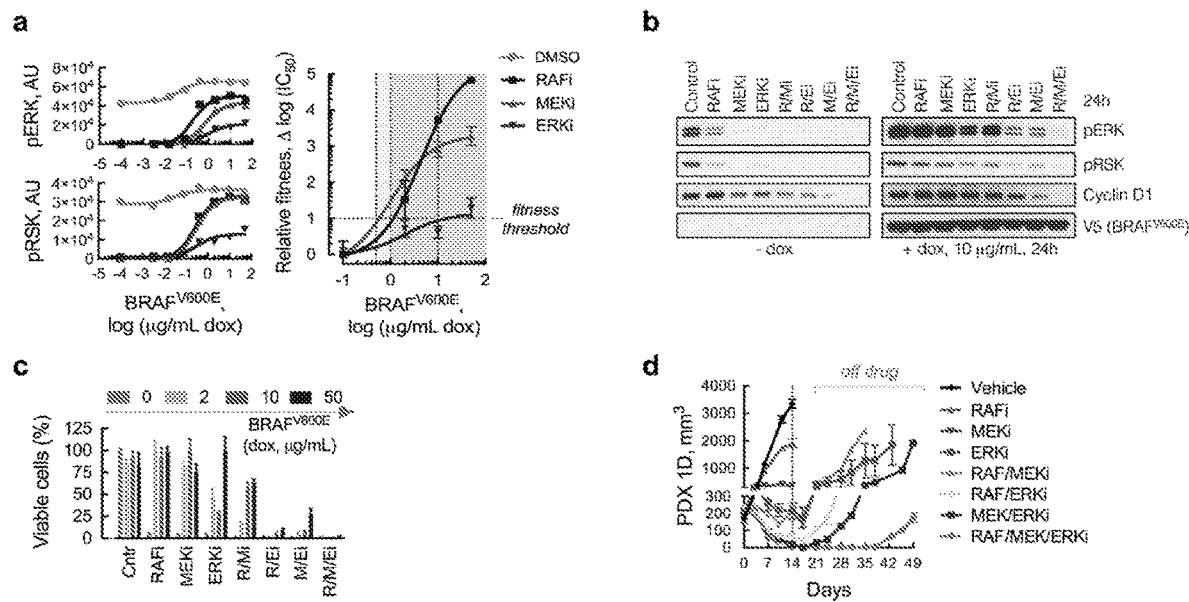
Fig. 3A-D

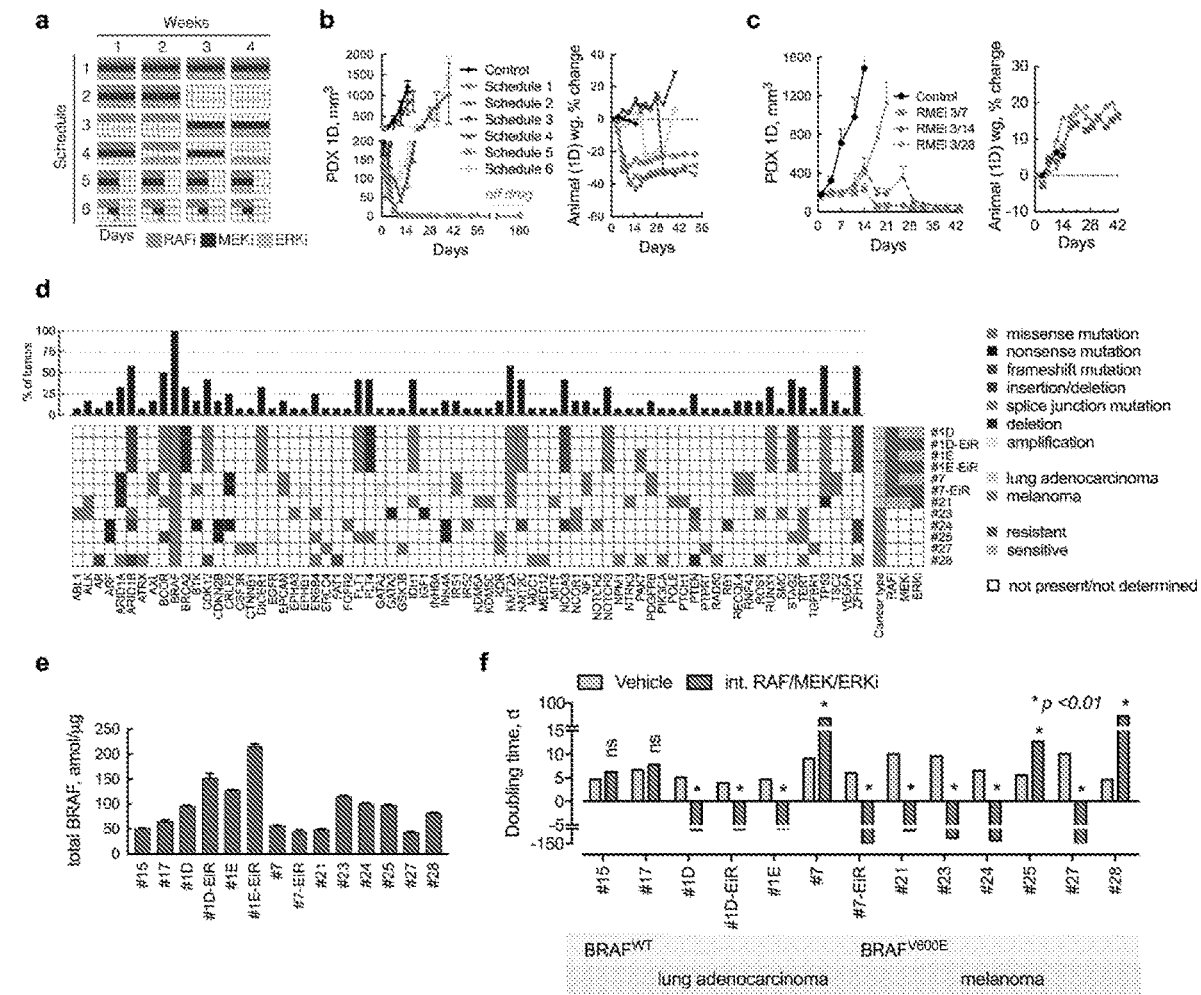
Fig. 4A-F

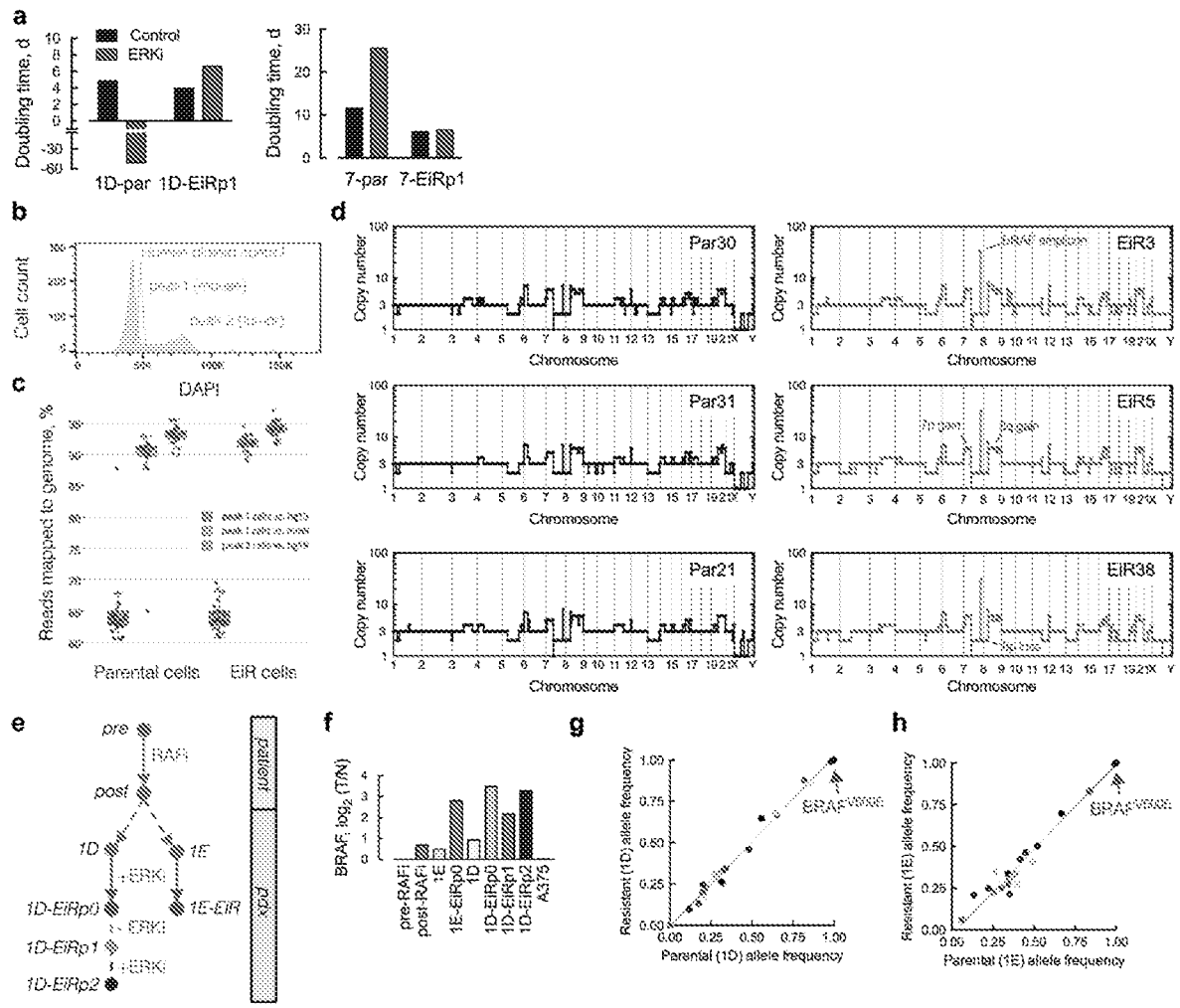
Fig. 5A-H

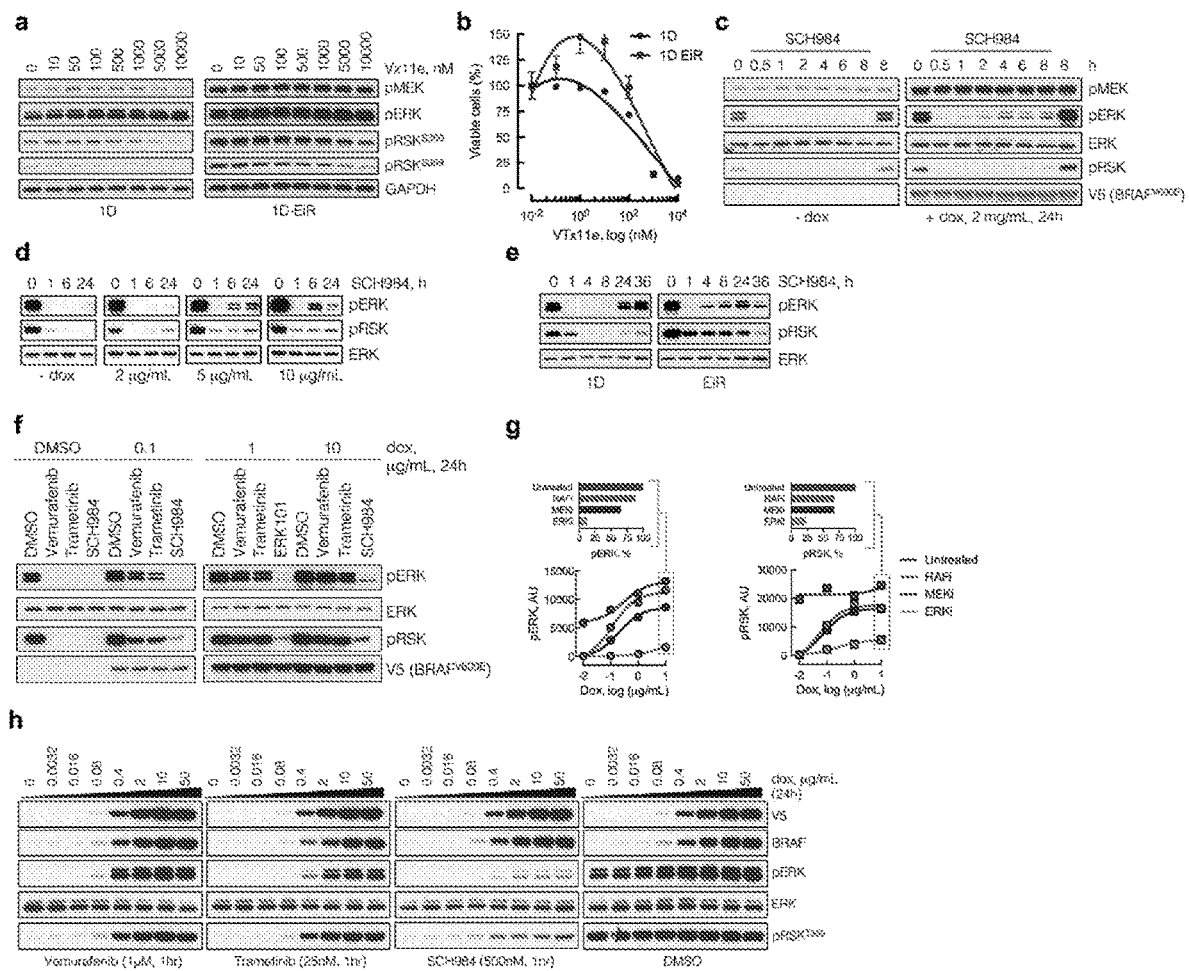
Fig. 6A-H

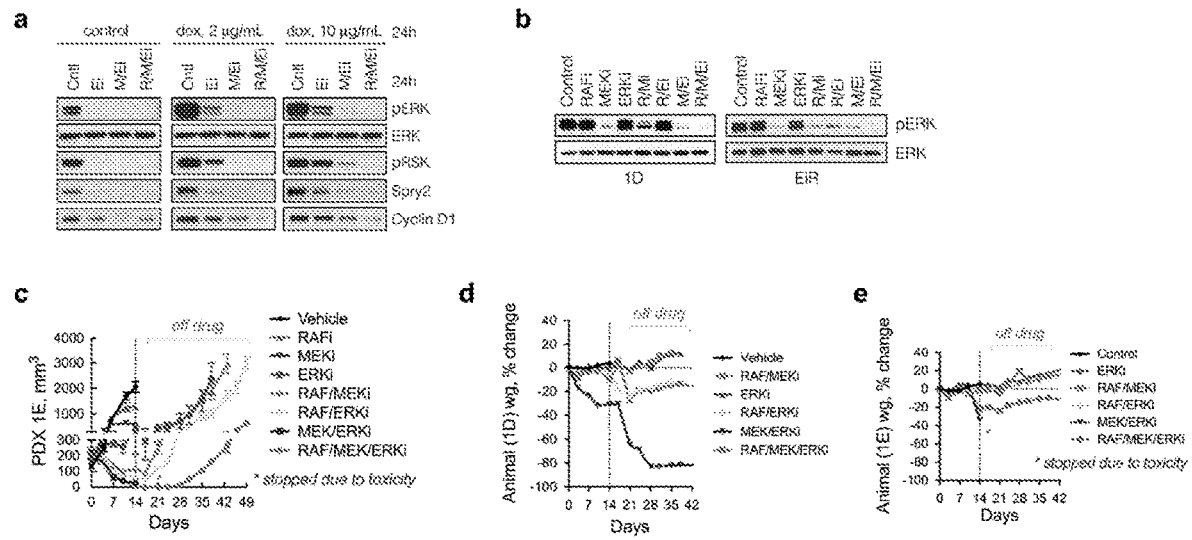
Fig. 7A-E

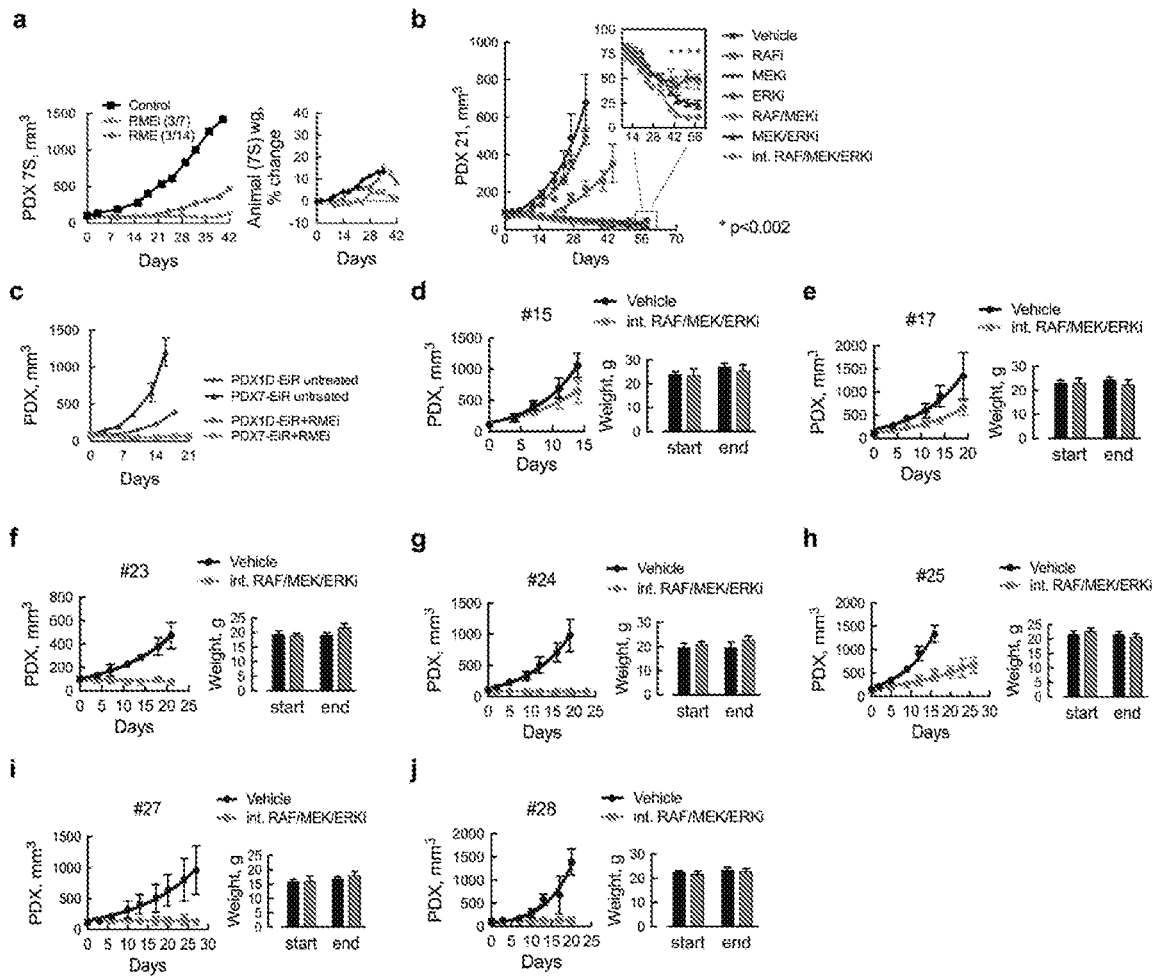
Fig. 8A-J

METHODS AND COMPOSITIONS FOR TREATMENT OF BRAF MUTANT CANCERS

CROSS-REFERENCE TO RELATED APPLICATIONS

This application claims the benefit of priority of U.S. Provisional Patent Application No. 62/432,608, filed on Dec. 11, 2016, the content of which is hereby incorporated by reference in its entirety.

STATEMENT REGARDING FEDERALLY SPONSORED RESEARCH

This invention was made with government support under grant number CA191082 awarded by the National Institutes of Health. The government has certain rights in the invention.

INCORPORATION BY REFERENCE

For the purposes of only those jurisdictions that permit incorporation by reference, all of the references cited in this disclosure are hereby incorporated by reference in their entireties. In addition, any manufacturers' instructions or catalogues for any products cited or mentioned herein are incorporated by reference. Documents incorporated by reference into this text, or any teachings therein, can be used in the practice of the present invention. Numbers in superscript or parentheses following text herein refer to the numbered references identified in the "Reference List" section of this patent application.

BACKGROUND

BRAF mutations occur in several tumor types, including approximately 10% of lung adenocarcinomas.[1,2] Of such BRAF mutations, approximately 98% are $BRAF^{V600E}$ mutations. The current therapy for $BRAF^{V600E}$ mutant tumors includes treatment with a RAF or MEK inhibitor, or a combination of these two agents. However, resistance to treatment is a frequent occurrence and not all patients exhibit a response to treatment. As such, almost all patients with metastatic $BRAF^{V600E}$ mutant cancer die from their disease. Thus, there is need for new and improved therapies for these patients. The present invention addresses this need.

SUMMARY OF THE INVENTION

The present invention is based, in part, on a series of important discoveries that are described in more detail in the Examples section of this patent specification. For example, it has now been discovered that a three-drug combination of a RAF inhibitor, a MEK inhibitor, and an ERK inhibitor effectively inhibits growth of $BRAF^{V600E}$ mutant tumors in vivo in a patient-derived xenograft (PDX) model—including tumors that exhibit either de novo or acquired resistance to inhibitors of ERK signaling. Furthermore, it has also been discovered that use of certain intermittent dosing schedules having alternating "treatment on" and "treatment off" times dramatically reduces toxicity of this drug combination. Building on these discoveries, and other discoveries presented herein, the present invention provides a variety of new and improved compositions and methods for the treatment of $BRAF^{V600E}$ mutant tumors.

For example, in some embodiments the present invention provides methods for treating BRAF mutant tumors, such methods comprising administering an effective amount of: (a) a RAF inhibitor, (b) a MEK inhibitor, and (c) an ERK inhibitor, to a subject having a tumor that comprises tumor cells having one or more BRAF mutations.

In some of such embodiments the tumor cells have a mutation in the activation segment of BRAF. In some of such embodiments the tumor cells have a mutation in the glycine-rich P loop of the N lobe of BRAF. In some of such embodiments the tumor cells have one or more mutations selected from the group consisting of: R461I, I462S, G463E, G463V, G465A, G465E, G465V, G468A, G468E, N580S, E585K, D593V, F594L, G595R, L596V, T598I, V599D, V599E, V599K, V599R, V600K, V600E, and A727V. In some of such embodiments the tumor cells have a $BRAF^{V600E}$ mutation.

In some of such embodiments the tumor is a melanoma. In some of such embodiments the tumor is a lung tumor. In some of such embodiments the tumor is selected from the group consisting of a papillary thyroid carcinoma, a colorectal tumor, a melanoma, a lung tumor (such as non-small-cell lung cancer tumor), a hairy cell leukaemia, an astrocytoma, an ameloblastoma, and a papillary craniopharyngioma.

In some of such embodiments the RAF inhibitor is selected from the group consisting of Dabrafenib (GSK2118436), Dabrafenib Mesylate (GSK-2118436 Mesylate), Encorafenib (LGX818), Vemurafenib (PLX4032, RG7204), Sorafenib, Sorafenib Tosylate, Zelboraf, Tafinlar, AZ 628, B-Raf IN 1, CEP-32496, CEP-32496 hydrochloride, GDC-0879, GW 5074, HG6-64-1, L-779450, LGX818, LY3009120, MLN 2480 (BIIB-024), PLX 4720, PLX7904, PLX8394, Sorafenib, Sorafenib Tosylate, R05126766 (CH5126766), RAF265 (CHIR-265), TAK-632, ZM 336372, SB590885, GW5074, and Raf265 derivative.

In some of such embodiments the MEK inhibitor is selected from the group consisting of Trametinib (Mekinist, GSK1120212), Cobimetinib (GDC-0973, RG7420), Selumetinib (AZD6244), Binimetinib (MEK162, ARRY-162, ARRY-438162), Pimasertib (AS-703026), Refametinib (RDEA119, Bay 86-9766), PD0325901, U0126-EtOH I, PD184352 (CI-1040), PD98059, BIX02189, GDC-0623, BI-847325, SL327, BIX02188, AZD8330, TAK-733, Honokiol, and PD318088.

In some of such embodiments the ERK inhibitor is selected from the group consisting of SCH984 (MK8353), Ulixertinib (BVD-523, VRT752271, VTx11e), SCH772984, ERK5-IN-1, XMD8-92, FR 180204, DEL-22379, GDC-0994, and VX-11e. In some of such embodiments the ERK inhibitor inhibits un-phosphorylated ERK. In some of such embodiments the ERK inhibitor inhibits phosphorylated ERK.

In some of such embodiments the subject has a BRAF mutant tumor that is resistant to treatment using either a RAF inhibitor, a MEK inhibitor, or an ERK inhibitor alone. In some of such embodiments the subject has a BRAF mutant tumor that is resistant to treatment using only two agents selected from the group consisting of a RAF inhibitor, a MEK inhibitor, and an ERK inhibitor. In some of such embodiments the subject has a BRAF mutant tumor that is resistant to treatment using only a RAF inhibitor and a MEK inhibitor. In each of such embodiments the resistance may be either de novo resistance or acquired resistance. In some of such embodiments the subject has a BRAF mutant tumor that comprises tumor cells having one or more mutations that have been associated with resistance to RAF inhibitors and/or MEK inhibitors, such as, for example, a NF1 mutation, a PTEN mutation, an IRS mutation, an EGFR mutation, and/or a TSC2 mutation.

In some of such embodiments the RAF inhibitor, the MEK inhibitor, and/or the ERK inhibitor are administered systemically. In some of such embodiments the RAF inhibitor, the MEK inhibitor, and/or the ERK inhibitor are administered locally.

In some of such embodiments the RAF inhibitor, the MEK inhibitor, and the ERK inhibitor are administered concurrently. In some of such embodiments the subject is treated with the RAF inhibitor, the MEK inhibitor, and the ERK inhibitor concurrently. In some of such embodiments the RAF inhibitor, the MEK inhibitor, and the ERK inhibitor are administered on the same day. In some of such embodiments the RAF inhibitor, the MEK inhibitor, and the ERK inhibitor are administered sequentially. In some of such embodiments the subject is treated with the RAF inhibitor, the MEK inhibitor, and the ERK inhibitor sequentially.

In some of such embodiments the MEK inhibitor, and the ERK inhibitor are administered using an intermittent dosing schedule. In some of such embodiments the intermittent dosing schedule comprises administering the RAF inhibitor, the MEK inhibitor, and the ERK inhibitor on only 3 out of every 7 days, for example on 3 consecutive days out of every 7 days. In some of such embodiments the intermittent dosing schedule comprises administering the RAF inhibitor, the MEK inhibitor, and the ERK inhibitor on only 4 out of every 7 days, for example on 4 consecutive days out of every 7 days. In some of such embodiments the intermittent dosing schedule comprises administering the RAF inhibitor, the MEK inhibitor, and the ERK inhibitor for only 1 out of every 2 weeks. In some embodiments such intermittent dosing schedules will result in intermittent inhibition of RAF, MEK, and ERK in the subject. In some embodiments such intermittent dosing schedules will result in levels of the RAF inhibitor, the MEK inhibitor, and the ERK inhibitor that vary in the subject's circulation or tumor over time resulting in intermittent inhibition of RAF, MEK, and ERK in the subject. For example, in some embodiments the intermittent dosing schedules will result in there being effective RAF inhibition, MEK inhibition, and ERK inhibition in the subject's tumor during only 3 out of every 7 days, or during only 4 out of every 7 days, or during only 1 week out of every 2 weeks, etc., approximately mirroring the intermittent dosing schedule used.

In some embodiments the intermittent dosing schedule comprises: (i) administering the RAF inhibitor, the MEK inhibitor, and the ERK inhibitor daily for 3 consecutive days, (ii) not administering the RAF inhibitor, the MEK inhibitor, and the ERK inhibitor daily for a period of 4 consecutive days immediately following step (i), and (iii) subsequently repeating steps (i) and (ii) one or more times. In other embodiments the intermittent dosing schedule comprises: (i) administering the RAF inhibitor, the MEK inhibitor, and the ERK inhibitor daily for 4 consecutive days, followed by (ii) a period of 3 consecutive days during which the RAF inhibitor, the MEK inhibitor, and the ERK inhibitor are not administered, and (iii) subsequently repeating steps (i) and (ii) one or more times. In yet other embodiments the intermittent dosing schedule comprises: (i) administering the RAF inhibitor, the MEK inhibitor, and the ERK inhibitor daily for 7 consecutive days, followed by (ii) a period of 7 consecutive days during which the RAF inhibitor, the MEK inhibitor, and the ERK inhibitor are not administered, and (iii) subsequently repeating steps (i) and (ii) one or more times In some embodiments the various treatment methods described herein may further comprise performing a diagnostic test to determine if the subject has a tumor that comprises tumor cells having one or more BRAF mutations. Typically, such a diagnostic test will be performed prior to administering the RAF inhibitor, MEK inhibitor, and ERK inhibitor. For example, in some embodiments, any of the treatment methods summarized above, or described elsewhere herein, may further comprising performing a diagnostic test to determine if the subject has a tumor that comprises a $BRAF^{V600E}$ mutation, prior to administering the RAF inhibitor, MEK inhibitor, and ERK inhibitor to the subject.

In addition to the various treatment methods provided herein, the present invention also provides various pharmaceutical compositions. For example, in some embodiments the present invention provides pharmaceutical compositions comprising: (a) a RAF inhibitor, (b) a MEK inhibitor, and (c) an ERK inhibitor. Similarly, in some embodiments the present invention provides pharmaceutical compositions for use in treatment of BRAF mutant tumors (such as $BRAF^{V600E}$ mutant tumors) such pharmaceutical compositions comprising: (a) a RAF inhibitor, (b) a MEK inhibitor, and (c) an ERK inhibitor. The present invention also provides methods of treatment comprising administering such pharmaceutical compositions to subjects having BRAF mutant tumors.

These and other aspects of the present invention are described further in the Detailed Description, Drawings, and Examples sections of this patent application. Furthermore, one of skill in the art will recognize that the various embodiments of the present invention described throughout this patent disclosure can be combined in various different ways, and that such combinations are within the scope of the present invention.

BRIEF DESCRIPTION OF THE DRAWINGS

FIG. 1A-L. ERK inhibitor-resistant populations emerge through a positive selection of cells with increased BRAFV600E expression. FIG. 1A—A schematic of this study's approach. FIG. 1B—Patient-derived xenografts (PDX) from patients with BRAFV600E-mutant lung cancer were treated with ERK inhibitor SCH984 (75 mpk) over time (n=5, mean±s.e.m). FIG. 1C—Copy number (CN) profiles in single cells derived from parental (Par) and ERK inhibitor-resistant (EiR) tumors. FIG. 1D-E—Projection of single cells into the top three principal components, collectively accounting for 92% of the CN variation. The cells are grouped according to their tumor of origin (FIG. 1D) or their CN cluster (FIG. 1E). FIG. 1F—A phylogenetic tree depicting the relationship of single cells derived from Par and EiR tumors, determined by Manhattan-Ward clustering of integer CN. Dots indicate cells with BRAF amplification in the top fifteen percent. FIG. 1G—The distribution of segment values spanning the BRAF allele in tumor and stromal cells. For stromal cells, sequenced reads were mapped to the mouse genome (see also FIG. 5E). FIG. 1H—Fluorescence in situ hybridization (FISH) analysis of Par and EiR tumors. Probes spanning BRAF or chromosome 7 centromere are shown (a representative of five different fields is shown). FIG. 1I—BRAF or centromere probes were quantified by manual counting (n=100, all data are shown). j, Extra-chromosomal localization of the BRAF gene (arrows) in an EiR cell undergoing metaphase. FIG. 1K—The expression of BRAFV600E protein in matched PDX1D and 1E tumor sets was determined by mass spectrometry (n=3, mean±s.e.m). Actin and tubulin were used as controls. FIG. 1L—The BRAF mRNA expression as a function of its CN in 145 untreated BRAFV600E-mutant melanomas. The data, and the designation of the CN status, were obtained from TCGA. Inset: The BRAF mRNA/CN status in BRAFV600E mutant melanoma PDX models used in this study. In all figures "n" represents biological replicates.

FIG. 2A-G. Increased BRAFV600E expression attenuates direct inhibition of ERK. FIG. 2A—Cell lines derived from parental (1D) or ERK inhibitor-resistant (1D-EiR) tumors were analyzed by immunoblotting to determine the expression level of BRAFV600E protein and the effect on phosphorylated and total ERK. FIG. 2B—The indicated cell lines were treated as shown for 1 h and cell extracts were evaluated to determine the effect on the signaling intermediates shown. A representative of at least two independent experiments is shown for the immunoblots in this figure. FIG. 2C—The indicated cells were treated for 72h followed by determination of viable cells by using the ATP-glow assay (n=3, mean±s.e.m). FIG. 2D—A model describing how BRAFV600E expression attenuates the effect of ERK inhibitor, which interacts poorly with activated (or phosphorylated) ERK. FIG. 2E—A375 cells engineered to express BRAFV600E-under a doxycycline (dox)-induced promoter were stimulated with increasing concentrations of dox, followed by treatment with the ERK inhibitor. FIG. 2F—As in FIG. 2D but the cells were treated with the ERK inhibitor for 48h after dox stimulation. FIG. 2G—A375, which are sensitive to the ERK inhibitor at baseline, were stimulated and treated as shown (n=3, mean±s.e.m). Note that withdrawal of dox after a 6-week stimulation restored sensitivity to the ERK inhibitor.

FIG. 3A-D. Co-targeting all three kinases in the MAPK cascade achieves durable inhibition of signaling and proliferation. FIG. 3A—A375 cells were stimulated with increasing concentrations of dox (24h), followed by treatment with ERK signaling inhibitors for 1 h (left) or 72h (right), to determine the effect on signaling or cell proliferation, respectively (n=3, mean±s.e.m). The relative fitness was defined as the difference in log(IC50) in the presence or absence of dox. The fitness threshold was defined as the BRAFV600E expression, required to increase the drug's log(IC50) by 1. FIG. 3B—As in FIG. 3A, but cells were treated with vemurafenib (RAFi, 1 µM), trametinib (MEKi, 25 nM) and/or SCH984 (ERKi, 500 nM) for 24h to determine the effect on ERK signaling intermediates. A representative of three independent experiments is shown. FIG. 3C—As in FIG. 3B, but cells were treated for 72h with to determine the effect on viability (n=3, mean±s.e.m). FIG. 3D—Mice bearing PDX 1D were treated with dabrafenib (RAFi, 30 mpk), trametinib (3 mpk) and/or SCH984 (75 mpk) as shown for 14 days followed by discontinuation of treatment to determine the effect on tumor growth (n=5 replicates, mean±s.e.m). Vemurafenib (alone or in combination) had a similar effect to dabrafenib (see below).

FIG. 4A-F. An intermittent combination treatment inhibits tumor growth in lung cancer and melanoma BRAFV600E PDX. FIG. 4A-B—A schematic representation (a) of several three-drug combination treatment schedules and their effect (b) on the growth of PDX1D tumors in athymic mice (n=5, mean±s.e.m). RAFi: vemurafenib, 50 mpk, MEKi: trametinib, 3 mpk, ERKi: SCH984, 75 mpk. The effect of drug treatment on animal weight was used as a marker of treatment toxicity (see Methods in Example 1). Mice treated on schedule 5 remained free of tumor for up to 180 days after drug discontinuation. FIG. 4C—Additional optimization of the off-drug interval to minimize toxicity, while retaining maximal tumor growth inhibition. FIG. 4D—The profile of genetic alterations in the BRAFV600E PDX models utilized in this study. FIG. 4E—The expression of total BRAF in the PDX models was determined using mass spectrometry (n=3, mean±s.e.m). FIG. 4F—The effect of the intermittent three drug combination treatment (administered on a 3/7-day schedule) on the doubling time of lung and melanoma PDX models (n=5, for each untreated or treated arms, mean; ns: p>0.05; primary data are shown in FIG. 8).

FIG. 5A-H. Characterization of ERK inhibitor-resistant PDX1 models. FIG. 5A—The parental PDX models shown, or their derivatives that grew in the presence of ERK inhibitor were treated with the drug to determine the emergence of resistant tumors. The effect on the doubling time is shown (n=5, mean). Par: parental, EiR: ERK-inhibitor resistant, p: passages in athymic mice. FIG. 5B—Single nuclei extracted from PDX1D tumors were analyzed by FACS to determine the distribution of cells according their DNA content. A human diploid cell line was used as a control. FIG. 5C—Genomic DNA extracted from near diploid (peak 1) or polyploid (peak 2) nuclei was amplified and subjected to sparse massively parallel sequencing. Sequencing reads were mapped to reference human or mouse genomes. FIG. 5D—A schematic of the treatment timeline and models derived from patient 1. FIG. 5E-G—Genomic DNA form the indicated cell line (A375), patient biopsies (pre, post) or PDX models was subjected to targeted next generation sequencing to determine BRAF CN (FIG. 5E) or single nucleotide mutations (FIG. 5F-G) before and after ERK inhibitor-treatment. The BRAFV600E allele frequency is suggestive of homozygous tumors.

FIG. 6A-H. Increased expression of BRAFV600E diminishes the sensitivity to ERK inhibitors. FIG. 6A—Tumor-derived cell lines (1D or 1D-EiR) were treated with the indicated concentrations of the ERK inhibitor V×11e for 1 h and cell extracts were evaluated by immunoblotting to determine the effect on the signaling intermediates shown. Unlike SCH984, VT×11e does not inhibit the phosphorylation of ERK. FIG. 6B—The indicated cells were treated for 72h to determine the effect on cell viability (n=3, mean±s.e.m). FIG. 6C-D—A375 cells engineered to express BRAFV600E under a dox-inducible promoter were stimulated with dox followed by ERK inhibitor treatment (500 nM) as shown. FIG. 6E—Cell lines 1D and EiR were treated with the SCH984 (500 nM) for the indicated times to determine pathway adaptation to the drug. FIG. 6F-H—Dox-stimulated A375 cells were treated for 1 h with inhibitors of ERK signaling (vemurafenib, 1 µM; trametinib 25 nM; SCH984, 500 nM) to determine the effect of BRAFV600E expression on the inhibition of ERK signaling intermediates (FIG. 6F, 6H). The degree of pathway inhibition was quantified by densitometry (FIG. 6G). A representative of at least two independent experiments is shown for the immunoblots in this figure.

FIG. 7A-E. Antitumor and toxicity profile of combination treatments utilizing ERK signaling inhibitors. FIG. 7A—Dox-stimulated A375 cells were treated for 24h with an ERK inhibitor alone or in combination with RAF and/or MEK inhibitors, at the concentrations described in FIG. 6. FIG. 7B—Tumor derived cell lines 1D and 1D-EiR were treated for 24h to determine the effect on ERK phosphorylation. FIG. 7C—Mice bearing PDX 1E were treated with dabrafenib (RAFi, 30 mpk), trametinib (3 mpk) and/or SCH984 (75 mpk) as shown for 14 days followed by discontinuation of treatment to determine the effect on tumor growth (n=5, mean±s.e.m). Mice treated with the MEK/ERKi combination experienced significant toxicity leading to discontinuation of the experiment. FIG. 7D-E—The effect of multidrug treatments on the weight of mice bearing 1D or 1E PDX models (see Methods in Example 1). Note that the addition of the RAF inhibitor decreased the toxicity associated with combined MEK/ERK inhibition. When considering that RAF inhibitors transactivate ERK signaling in cells with BRAFWT, it is possible that the RAF inhibitor counteracts the effect of the MEK/ERK inhibitors in normal tissue, thus reducing the toxicity of the three-drug combination.

FIG. 8A-J. The effect of the intermittent combination therapy on lung cancer and melanoma BRAFV600E PDX models. Mice bearing the indicated tumors were treated with vemurafenib (50 mpk), trametinib (3 mpk) and SCH984 (75 mpk) as indicated to determine the effect on tumor growth and animal weight. FIG. 8A—Optimization of the three-drug intermittent administration scheme. FIG. 8B—Effect of the intermittent combination administered on a three-days-on/four-days-off schedule in a model with de novo resistance to ERK inhibitor treatment. FIG. 8C—The effect of treatment in models with acquired resistance to the ERK inhibitor. FIG. 8D-E—PDX models harboring wild type BRAF. FIG. 8F-J—PDX models derived from patients with BRAFV600E mutant melanoma. The weight at the onset and termination of treatment is shown. For all panels, n=5, mean±s.e.m; p: unpaired two-tailed t test between MEK/ERKi and int. RAF/MEK/ERKi-treated tumors.

DETAILED DESCRIPTION

While some of the main embodiments of the present invention are described in the above Summary of the Invention and in the Examples and Claims sections of this patent application, this Detailed Description section provides certain additional description relating to the compositions and methods of the present invention, and is intended to be read in conjunction with all other sections of the present patent application.

Definitions and Abbreviations

As used in this specification and the appended claims, the singular forms "a," "an," and "the" include plural referents, unless the context clearly dictates otherwise. The terms "a" (or "an") as well as the terms "one or more" and "at least one" can be used interchangeably.

Furthermore, "and/or" is to be taken as specific disclosure of each of the two specified features or components with or without the other. Thus, the term "and/or" as used in a phrase such as "A and/or B" is intended to include A and B, A or B, A (alone), and B (alone). Likewise, the term "and/or" as used in a phrase such as "A, B, and/or C" is intended to include A, B, and C; A, B, or C; A or B; A or C; B or C; A and B; A and C; B and C; A (alone); B (alone); and C (alone).

Units, prefixes, and symbols are denoted in their Système International de Unites (SI) accepted form. Numeric ranges provided herein are inclusive of the numbers defining the range.

Where a numeric term is preceded by "about" or "approximately," the term includes the stated number and values ±20% of the stated number.

Numbers in parentheses or superscript following text in this patent disclosure refer to the numbered references provided in the "Reference List" section at the end of this patent disclosure.

Wherever embodiments are described with the language "comprising," otherwise analogous embodiments described in terms of "consisting of" and/or "consisting essentially of" are included.

As used herein the abbreviation "BRAF" may be used to refer to either a B-Raf serine/threonine-protein kinase protein, or a BRAF gene that encodes the B-Raf kinase protein. It will be clear from the context in which the term is used whether the gene, the protein, or both, are referred to.

As used herein the abbreviation "BRAF$^{V600E}$", may be used to refer to either a mutated form of the BRAF gene that encodes a B-Raf serine/threonine-protein kinase having a V600E mutation, or a mutated form of a B-Raf serine/threonine-protein kinase having a V600E mutation. It will be clear from the context in which the term is used whether the gene, the protein, or both, are referred to. "V600E" refers to a mutation that results in a valine (V) being substituted by a glutamate (E) at amino acid position 600 in the BRAF protein.

As used herein the abbreviation "RAF" may be used to refer to either a RAF proto-oncogene serine/threonine-protein kinase protein, or the RAF gene that encodes the kinase protein. It will be clear from the context in which the term is used whether the gene, the protein, or both are referred to. For example, the term RAF inhibitor refers to inhibitors of the RAF protein (i.e. the RAF serine/threonine-protein kinase).

As used herein the abbreviation "MEK" may be used to refer to either a mitogen-activated protein kinase kinase protein, or the MEK gene that encodes the kinase protein. It will be clear from the context in which the term is used whether the gene, the protein, or both are referred to. For example, the term MEK inhibitor refers to inhibitors of the MEK protein (i.e. the mitogen-activated protein kinase kinase).

As used herein the abbreviation "ERK" may be used to refer to either an extracellular signal-regulated kinase protein, or the ERK gene that encodes the kinase protein. It will be clear from the context in which the term is used whether the gene, the protein, or both are referred to. For example, the term ERK inhibitor refers to inhibitors of the ERK protein (i.e. the extracellular signal-regulated kinase protein).

As used herein the abbreviation 'PDX" refers to a patient-derived xenograft.

As used herein the abbreviation "IP" refers to intraperitoneal.

As used herein the abbreviation "IT: refers to intratumoral. For example, a drug injected directly into a tumor is delivered intratumorally.

As used herein the abbreviation "IV" refers to intravenous. It is common to administer agents to mice via an IP route, which is considered to be analogous to administering an agent to a human subject by an IV route.

As used herein the terms "inhibiting" and "blocking" are used interchangeably, as are the terms "inhibit" or "block" and the terms "inhibitor" or "blocker." The terms "inhibit" and "block" refer to any statistically significant decrease in a given biological activity.

Other abbreviations and definitions may be provided elsewhere in this patent specification, or may be well known in the art.

Active Agents for Use in the Compositions and Methods of the Invention

The methods and compositions provided by present invention involve various different active agents, including, but not limited to, RAF inhibitors, MEK inhibitors, and ERK inhibitors.

In those embodiments of the present invention that involve RAF inhibitors, any suitable RAF inhibitor known in the art may be used. In some embodiments the RAF inhibitor is selected from the group consisting of: Dabrafenib (GSK2118436), Dabrafenib Mesylate (GSK-2118436 Mesylate), Encorafenib (LGX818), Vemurafenib (PLX4032, RG7204), Sorafenib, Sorafenib Tosylate, Zelboraf, Tafinlar, AZ 628, B-Raf IN 1, CEP-32496, CEP-32496 hydrochloride, GDC-0879, GW 5074, HG6-64-1, L-779450, LGX818, LY3009120, MLN 2480 (BIIB-024), PLX 4720, PLX7904, PLX8394, Sorafenib, Sorafenib Tosylate, RO5126766 (CH5126766), RAF265 (CHIR-265), TAK-632, ZM 336372, SB590885, GW5074, and Raf265 derivative.

In those embodiments of the present invention that involve MEK inhibitors, any suitable MEK inhibitor known in the art may be used. In some embodiments the MEK inhibitor is selected from the group consisting of: Trametinib (Mekinist, GSK1120212), Cobimetinib (GDC-0973, RG7420), Selumetinib (AZD6244), Binimetinib (MEK162, ARRY-162, ARRY-438162), Pimasertib (AS-703026), Refametinib (RDEA119, Bay 86-9766), PD0325901, U0126-EtOH I, PD184352 (CI-1040), PD98059, BIX02189, GDC-0623, BI-847325, SL327, BIX02188, AZD8330, TAK-733, Honokiol, and PD318088.

In those embodiments of the present invention that involve ERK inhibitors, any suitable ERK inhibitor known in the art may be used. In some embodiments the ERK inhibitor is selected from the group consisting of: SCH984 (MK8353), Ulixertinib (BVD-523, VRT752271, VTx11e), SCH772984, ERK5-IN-1, XMD8-92, FR 180204, DEL-22379, GDC-0994, and VX-11e.

One of ordinary skill in the art will appreciate that, in addition to the various specified active agents referred to above or elsewhere herein, the compositions and methods of the present invention can, in some instances, also be carried out using analogues, homologues, variants, or derivatives of such specified active agents if, and provided that, such analogues, homologues, variants, or derivatives retain the key functional properties of the specified active agents. For example, one of ordinary skill in the art will appreciate that an analogue, homologue, variant, or derivative of a specified RAF inhibitor can be used provided that it retains RAF inhibitor activity. Similarly, one of ordinary skill in the art will appreciate that an analogue, homologue, variant, or derivative of a specified MEK inhibitor can be used provided that it retains MEK inhibitor activity, and that an analogue, homologue, variant, or derivative of a specified ERK inhibitor can be used provided that it retains ERK inhibitor activity.

Compositions

In certain embodiments, the present invention provides compositions, such as pharmaceutical compositions. The term "pharmaceutical composition," as used herein, refers to a composition comprising at least one active agent as described herein, and one or more other components useful in formulating a composition for delivery to a subject, such as diluents, buffers, carriers, stabilizers, dispersing agents, suspending agents, thickening agents, excipients, preservatives, and the like.

Methods of Treatment, Dosing Regimens & Subjects

In certain embodiments the present invention provides methods of treatment. As used herein, the terms "treat," "treating," and "treatment" encompass achieving, and/or performing a method that achieves, a detectable improvement in one or more clinical indicators or symptoms associated with a BRAF mutant tumor. For example, such terms include, but are not limited to, reducing the rate of growth of a BRAF mutant tumor (or of tumor cells), halting the growth of a BRAF mutant tumor (or of tumor cells), causing regression of a BRAF mutant tumor (or of tumor cells), reducing the size of a BRAF mutant tumor (for example as measured in terms of tumor volume or tumor mass), reducing the grade of a BRAF mutant tumor, eliminating a BRAF mutant tumor (or tumor cells), preventing, delaying, or slowing recurrence (rebound) of a BRAF mutant tumor, improving symptoms associated with a BRAF mutant tumor, improving survival from a BRAF mutant tumor, inhibiting or reducing spreading of a BRAF mutant tumor (e.g. metastases), and the like.

As used herein the term "subject" encompasses all mammalian species, including, but not limited to, humans, non-human primates, dogs, cats, rodents (such as rats, mice and guinea pigs), cows, pigs, sheep, goats, horses, and the like—including all mammalian animal species used in animal husbandry, as well as animals kept as pets and in zoos, etc. In some embodiments the subjects are human.

In some embodiments the present methods and compositions can be used to treat any BRAF mutant tumor in a subject. In some embodiments the subject's tumor cells may have a mutation in the activation segment of BRAF. In some embodiments the subject's tumor cells may have a mutation in the glycine-rich P loop of the N lobe of BRAF. In some embodiments the subject's tumor cells may have one or more mutations selected from the group consisting of: R461I, I462S, G463E, G463V, G465A, G465E, G465V, G468A, G468E, N580S, E585K, D593V, F594L, G595R, L596V, T598I, V599D, V599E, V599K, V599R, V600K, V600E, and A727V. In some embodiments the subject's tumor cells have a BRAF$^{V600E}$ mutation.

In some embodiments the subject has a BRAF-mutant melanoma. In some embodiments the subject has a BRAF-mutant lung tumor. In some embodiments the subject has a BRAF-mutant tumor selected from the group consisting of a papillary thyroid carcinoma, a colorectal tumor, a melanoma, a lung tumor (such as non-small-cell lung cancer tumor), a hairy cell leukaemia, an astrocytoma, an ameloblastoma, and a papillary craniopharyngioma.

In some embodiments the subject has a tumor that is resistant to treatment using only two agents selected from the group consisting of a RAF inhibitor, a MEK inhibitor, and an ERK inhibitor. In some embodiments the subject has a tumor that resistant to treatment using only a RAF inhibitor and a MEK inhibitor. In some embodiments the subject has a tumor that comprises tumor cells having one or more mutations that have been associated with resistance to RAF inhibitors and/or MEK inhibitors, such as, for example, a NF1 mutation, a PTEN mutation, an IRS mutation, an EGFR mutation, and/or a TSC2 mutation. As used herein, the terms "resistant" and "resistance" are used consistent with their normal usage in the art and consistent with the understanding of those term by physicians who treat cancer (e.g. oncologists). For example, consistent with its usual meaning in the art, a tumor or a subject may be considered "resistant" to a certain agent (or combination of agents), or "resistant" to treatment with a certain agent (or combination of agents), if, despite administration of that agent (or combination of agents), a subject's tumor (or tumor cells) grows, and/or progresses, and/or spreads, and/or metastasizes, and/or recurs. In some instances, a tumor may initially be sensitive to treatment with a certain agent (or combination of agents), but later became resistant to treatment with such agent (or combination of agents).

In some embodiments the subject has a BRAF mutant tumor that has recurred following a prior treatment with other compositions or methods, including, but not limited to, chemotherapy, radiation therapy, or surgical resection, or any combination thereof.

In some embodiments the subject has a BRAF mutant tumor that has not previously been treated.

As used herein the terms "effective amount" or "therapeutically effective amount" refer to an amount of an active agent as described herein that is sufficient to achieve, or contribute towards achieving, one or more desirable clinical outcomes, such as those described in the "treatment" description above. An appropriate "effective" amount in any individual case may be determined using standard techniques known in the art, such as dose escalation studies, and may be determined taking into account such factors as the desired route of administration (e.g. systemic vs. intratumoral), desired frequency of dosing, etc. Furthermore, an "effective amount" may be determined in the context of any co-administration method to be used. One of skill in the art can readily perform such dosing studies (whether using single agents or combinations of agents) to determine appropriate doses to use, for example using assays such as those described in the Examples section of this patent application—which involve administration of the agents described herein to subjects (such as animal subjects routinely used in the pharmaceutical sciences for performing dosing studies).

For example, in some embodiments the dose of an active agent of the invention may be calculated based on studies in humans or other mammals carried out to determine efficacy and/or effective amounts of the active agent. The dose may be determined by methods known in the art and may depend on factors such as pharmaceutical form of the active agent, route of administration, whether only one active agent is used or multiple active agents (for example, the dosage of a first active agent required may be lower when such agent is used in combination with a second active agent), and patient characteristics including age, body weight or the presence of any medical conditions affecting drug metabolism.

In those embodiments described herein that refer to specific doses of agents to be administered based on mouse studies, one of skill in the art can readily determine comparable doses for human studies based on the mouse doses, for example using the types of dosing studies and calculations known in the art and/or described herein.

In some embodiments suitable doses of the various active agents described herein can be determined by performing dosing studies of the type that are standard in the art, such as dose escalation studies, for example using the dosages shown to be effective in mice in the Examples section of this patent application as a starting point.

In some embodiments one or more of the active agents is used at approximately its maximum tolerated dose, for example as determined in phase I clinical trials and/or in dose escalation studies. In some embodiments one or more of the active agents is used at about 90% of its maximum tolerated dose. In some embodiments one or more of the active agents is used at about 80% of its maximum tolerated dose. In some embodiments one or more of the active agents is used at about 70% of its maximum tolerated dose. In some embodiments one or more of the active agents is used at about 60% of its maximum tolerated dose. In some embodiments one or more of the active agents is used at about 50% of its maximum tolerated dose. In some embodiments one or more of the active agents is used at about 50% of its maximum tolerated dose. In some embodiments one or more of the active agents is used at about 40% of its maximum tolerated dose. In some embodiments one or more of the active agents is used at about 30% of its maximum tolerated dose.

In carrying out the treatment methods described herein, any suitable method or route of administration can be used to deliver the active agents or combinations thereof described herein. In some embodiments systemic administration may be employed, for example, oral or intravenous administration, or any other suitable method or route of systemic administration known in the art. In some embodiments intratumoral delivery may be employed. For example, the active agents described herein may be administered either systemically or locally by injection, by infusion through a catheter, using an implantable drug delivery device, or by any other means known in the art.

The present invention also provides certain novel "intermittent dosing schedules" that have been optimized to maximize anti-tumor efficacy while minimizing toxicity. Such "intermittent dosing schedules" comprise both: (a) times when an effective amount of each of the active agents is present in the subject or in the subject's tumor ("Treatment On" times), and (b) times when the active agents are not present in the subject or in the subject's tumor, or when an effective amount of each of the active agents is not present in the subject or in the subject's tumor ("Treatment Off" times). The "Treatment On" and "Treatment Off" times are alternated for the duration of the entire treatment period. The length of the entire treatment period can be varied, for example as determined by the subject's physician(s). Typically, the treatment period will be continued until a desired clinical outcome is achieved. For example, in some embodiments the entire treatment period may be about 1 month, about 2 months, about 3 months, about 4 months, about 5 months, about 6 months, about 7 months, about 8 months, about 9 months, about 10 months, about 11 months, about 12 months, about 14 months, about 16 months, about 18 months, about 20 months, about 22 months, about 24 months, about 30 months, about 36 months, or longer. The length of the "Treatment On" and "Treatment Off" times can also be varied, for example as determined by the subject's physician(s). Exemplary lengths of the "Treatment On" and "Treatment Off" times are provided below and in the Examples section of this patent application.

In each of such "intermittent dosing schedules" the subject is treated with the RAF inhibitor, the MEK inhibitor, and the ERK inhibitor concurrently during the "Treatment On" time(s). As used herein, the term "concurrently" does not require that the different agents are administered to the subject at precisely the same time. All that is required is that the agents are administered to the subject in such a way that there is effective inhibition of each of RAF, MEK, and ERK in the subject at approximately the same time. This is as opposed to a "sequential" treatment regimen whereby there might be, for example, effective inhibition of only RAF in the subject at a given time, and then at a different time (for example days or weeks later) there is effective inhibition only MEK and/or only ERK—without effective inhibition of RAF, etc. Concurrent treatment of a subject with a RAF inhibitor, a MEK inhibitor, and an ERK inhibitor may be achieved in a variety of different ways, including, for example, by: (a) administering to a subject a composition that comprises all three active agents, (b) administering all three active agents to a subject at the same time, or within minutes or hours of one another, or (c) by using one or more systems or devices designed to achieved sustained, timed, or delayed delivery of the active agents to the subject such that an effective amount of each of the active agents is present in the subject or in the subject's tumor at approximately the same time. In some embodiments the concurrent treatment comprises administering to a subject a composition that comprises all three active agents. In some embodiments the concurrent treatment comprises administering all three active agents to a subject at the same time. In some embodiments the concurrent treatment comprises administering all three active agents to a subject within minutes of one another. In some embodiments the concurrent treatment comprises administering all three active agents to a subject within a 30-minute window. In some embodiments the concurrent treatment comprises administering all three active agents to a subject within a 1-hour window. In some embodiments the concurrent treatment comprises administering all three active agents to a subject within a 2-hour window. In some embodiments the concurrent treatment comprises administering all three active agents to a subject within a 3-hour window. In some embodiments the concurrent treatment comprises administering all three active agents to a subject within a 4-hour window. In some embodiments the concurrent treatment comprises administering all three active agents to a subject within a 5-hour window. In some embodiments the concurrent treatment comprises administering all three active agents to a subject within a 6-hour window. In some embodiments the concurrent treatment comprises administering all three active agents to a subject within an 8-hour window. In some embodiments the concurrent treatment comprises administering all three active agents to a subject within a 10-hour window. In some embodiments the concurrent treatment comprises administering all three active agents to a subject within a 12-hour window. In some embodiments the concurrent treatment comprises administering all three active agents to a subject within an 18-hour window. In some embodiments the concurrent treatment comprises administering all three active agents to a subject within a 24-hour window. One of skill in the art will appreciate that there are a variety of different methods by which such "concurrent" treatment could be achieved, and all of such methods are encompassed herein.

Some exemplary dosing schedules are illustrated schematically in FIG. 4A. Schedules 2, 5, and 6 in FIG. 4A are "intermittent dosing schedules"—having both periods of concurrent treatment with all 3 active agents present ("Treatment On" times), and periods with no treatment with the active agents ("Treatment Off" times). The data provided in FIGS. 4B-C shows that the length of the "Treatment On" and "Treatment Off" times can be varied while still generating the desired effect of good treatment efficacy with minimal toxicity. FIG. 4B shows that, of the dosing schedules tested, treatment for 14 out of 28 days (14 days on 14 days off) and 4 out of 7 days (4 days on 3 days off) was effective. FIG. 4C shows that, of the dosing schedules tested, treatment for 3 out of 7 days or 3 out of 14 days was effective with minimal toxicity.

Additional, exemplary dosing schedules are described in the Examples section of this patent application—in both Example 1 and Example 2.

In some embodiments the "Treatment On" time is about 1 day, or 2 consecutive days, or 3 consecutive days, or 4 consecutive days, or 5 consecutive days, or 6 consecutive days, or 7 consecutive days, or 8 consecutive days, or 9 consecutive days, or 10 consecutive days, or 11 consecutive days, or 12 consecutive days, or 13 consecutive days, or 14 consecutive days, or 16 consecutive days, or 18 consecutive days, or 20 consecutive days, or 22 consecutive days, or 24 consecutive days, or 26 consecutive days, or 28 consecutive days.

In some embodiments the "Treatment Off" time is about 1 day, or 2 consecutive days, or 3 consecutive days, or 4 consecutive days, or 5 consecutive days, or 6 consecutive days, or 7 consecutive days, or 8 consecutive days, or 9 consecutive days, or 10 consecutive days, or 11 consecutive days, or 12 consecutive days, or 13 consecutive days, or 14 consecutive days, or 16 consecutive days, or 18 consecutive days, or 20 consecutive days, or 22 consecutive days, or 24 consecutive days, or 26 consecutive days, or 28 consecutive days.

The precise timing of the "Treatment On" and "Treatment Off" times can be adjusted and optimized by performing studies of the type demonstrated in the Examples section of this patent application as a starting point. In certain embodiments the compositions and methods of treatment provided herein may be employed together with other compositions and treatment methods known to be useful for tumor therapy, including, but not limited to, surgical methods (e.g. for tumor resection), radiation therapy methods, treatment with chemotherapeutic agents, treatment with antiangiogenic agents, or treatment with tyrosine kinase inhibitors. Similarly, in certain embodiments the methods of treatment provided herein may be employed together with procedures used to monitor disease status/progression, such as biopsy methods and diagnostic methods (e.g. MRI methods or other imaging methods).

For example, in some embodiments the agents and compositions described herein may be administered to a subject prior to performing surgical resection of a tumor, for example in order to shrink a tumor prior to surgical resection. In other embodiments the agents and compositions described herein may be administered both before and after performing surgical resection of a tumor.

In some embodiments the treatment methods described herein may be employed in conjunction with performing a diagnostic test to determine if the subject has a tumor that comprises tumor cells having one or more BRAF mutations, such as a $BRAF^{V600E}$ mutation. Any suitable diagnostic tests known in the art can be used. For example, there are several $BRAF^{V600E}$ diagnostic test kits and $BRAF^{V600E}$ diagnostic reagents (such as antibodies) that are either commercially available or in development, and any of these can be used. These include, but are not limited to, the Cobas 4800 BRAF V600 Mutation Test from Roche Molecular Diagnostics, and the THxID BRAF test from BioMerieux.

EXAMPLES

The invention is further described by the following non-limiting "Examples," as well as the Figures referred to therein and the descriptions of such Figures provided above.

Example 1

Treatment of $BRAF^{V600E}$-Mutant Tumors In Vivo Using Patient-Derived Xenograft Model Inhibition of RAF, alone or together with MEK, is effective in slowing the progression of $BRAF^{V600E}$-mutant melanomas and lung cancers[1-9], yet most patients still die from their disease. Durable suppression of ERK signaling is required for maximal antitumor effect and acquired resistance to these drugs is often associated with reactivated ERK[10,11]. Direct ERK inhibitors are thus undergoing clinical testing in an effort to improve patient outcomes. Here we used single-cell sequencing to model the evolution of $BRAF^{V600E}$-amplified subpopulations, which overcome the selective pressure of an ERK inhibitor in patient-derived xenograft (PDX) models. The level of $BRAF^{V600E}$ expression required for continued proliferation in the presence of the drug, i.e. fitness threshold, differed for RAF, MEK and ERK inhibitors. Concurrent targeting of these kinases, however, maximally inhibited ERK signaling and $BRAF^{V600E}$-amplified tumor growth. Administered on an intermittent schedule, this combination inhibited tumor growth in eleven $BRAF^{V600E}$-mutant PDX models, harboring distinct genetic co-alterations. This work provides insight into how resistance-causing alterations are selected and propagated during targeted therapy, and derives a therapeutic approach with the potential to durably inhibit tumor growth in patients.

BRAF mutations occur in ~10% of lung adenocarcinomas (LUAD)[12] but preclinical models are sparse. Tumor specimens from $BRAF^{V600E}$-mutant lung cancer patients with progressive disease on RAF inhibitor treatment were used to establish patient-derived xenograft (PDX) models (Table I). These were then used to study the therapeutic potential of extracellular signal regulated kinase (ERK) inhibition as shown in FIG. 1A. The ATP-competitive inhibitor SCH984 inhibits the kinase activity of ERK and prevents its phosphorylation by MEK[13,14]. SCH984 inhibited growth in 3/4 PDX tested (FIG. 1B) and the duration of response lasted several weeks. The tumors that grew on ERKi-treatment had diminished sensitivity to this drug in subsequent passages (FIG. 5A). Thus, ERKi-monotherapy in $BRAF^{V600E}$-mutant lung cancer is limited by acquired and de-novo resistance.

cells displaying chromosomal gains in 6p, 7p, 8q, 16q and 20, as well as losses in 1p, 7q and 8p, some of which are known to recur in lung adenocarcinoma genomes[18]. Heterogeneous alterations were identified on chromosomes 1p, 2p, 11q, 13 and X. This genetic diversity enabled the discrimination of parental from resistant cells in principal component analysis (FIG. 1D) and the inference of distinct subpopulations (A-E, FIGS. 1C, E and F). Subpopulations A, B and C comprised predominantly of parental cells; each intermixed with a few cells derived from the resistant tumor (FIGS. 1C and F). In contrast, subpopulation E consisted entirely of cells from the resistant tumor with the exception of a single parental cell (Par24), which is likely an earlier precursor of this dominant resistant clone.

Parental and resistant tumor cells had differences in the value of the segments spanning the BRAF locus (FIG. 1G). While nearly 50% of resistant cells had values greater than 6, no parental cells surpassed this threshold. Resistant cells with high BRAF values were largely confined to subpopulation E (FIG. 1F—dots). A few such cells, however, were also observed in other clusters, intermingled with parental cells, suggesting a trend towards parallel acquisition of more BRAF alleles. By comparison, stromal cells had a lower and homogeneous distribution of BRAF segment values (FIG. 1G). Bulk sequencing of patient biopsy specimens revealed a low-level gain in BRAF CN after exposure to a RAF inhibitor, with a more pronounced amplification emerging after treatment of PDX models with the ERKi (FIG. 5E,F). The allele frequency of single nucleotide mutations found in these tumors was not affected by ERKi-treatment (FIG. 5G, H).

Fluorescence in situ hybridization (FISH) confirmed a high-level BRAF amplification in EiR tumors, as well as the presence of cells with extra copies of BRAF in the parental populations (FIG. 1H). In EiR cells, however, the increase in

TABLE 1

Characteristics of lung cancer and melanoma patient-derived xenograft models

| Pt | PDX | Age/Sex | Cancer | Stage | Site | BRAF | Treatment history |
|---|---|---|---|---|---|---|---|
| 1 | 1D | 65/M | LUAD | IV | Pericardium | V600E | Chemo, RAFi |
|   | 1E | " | LUAD | IV | Effusion | V600E | Chemo, RAFi |
| 2 | 7 | 57/M | LUAD | IV | RML | V600E, K601Δ | Chemo, RAFi |
| 3 | 15 | 62/M | LUAD | IV | Effusion | WT | Chemo |
| 4 | 17 | 73/F | LUAD | IIIA | RLL | WT | Chemo |
| 5 | 21 | 64/M | LUAD | IV | LN | V600E | XRT, Chemo, RAFi |
| 6 | 23 | 42/F | Melanoma | IIIC | LN | V600E | Naïve |
| 7 | 24 | 67/M | Melanoma | IV | Mesentery | V600E, V600M | RAFi |
| 8 | 25 | 42/F | Melanoma | IV | Spleen | V600E | MEKi |
| 9 | 27 | 66/F | Melanoma | IV | SubQ | V600E | RAFi |
| 10 | 28 | 39/F | Melanoma | IV | LN | V600E | Naïve |

Modeling the emergence of ERK inhibitor-resistance (EiR) in one of these tumors might enable the determination of a better treatment approach. To this end, we performed bulk and/or single-cell sequencing in a matched parental and EiR tumor set. In the latter, genomic DNA from flow-sorted single nuclei was amplified by whole-genome amplification and subjected to sparse massively parallel sequencing, as described[15-17]. Compared to a human diploid control, PDX nuclei distributed in near-diploid and polyploid populations (Extended data FIG. 1B). Mapping of sequencing reads to the mouse or human genome revealed that these consisted of mouse stromal cells or human tumor cells, respectively (FIG. 5C).

The copy number (CN) profiles of the human tumors were complex (FIG. 1C and FIG. 5D), with almost all sequenced BRAF CN was greater than the increase in centromere copies (FIG. 1I), and the BRAF gene was dispersed in extra-chromosomal regions (FIG. 1J). As expected, this amplification led to an increased protein expression (FIG. 1K), determined by a novel mass spectrometry assay detecting $BRAF^{V600E}$ in paraffin-embedded tissue. These findings suggest that cells with $BRAF^{V600E}$ amplification overcome the selective pressure of consecutive exposure to ERK signaling inhibitors, leading to resistant tumors with increased expression of the $BRAF^{V600E}$-oncoprotein. BRAF CN gains or low-level amplifications were prevalent in patients with melanoma before exposure to targeted therapy (FIG. 1I), suggesting that these tumors are primed to overcome the effect of RAF[19-21] and that of ERK-inhibitors.

For positive selection to occur, increased expression of $BRAF^{V600E}$ must overcome ERKi-treatment and confer a growth advantage (i.e. fitness). This was tested in cell lines established from PDX1D and PDX1D-EiR models, which also exhibited a difference in $BRAF^{V600E}$ expression (FIG. 2A). ERKi-treatment suppressed signaling and proliferation less potently in 1D-EiR than in 1D cells, as evidenced by the residual phosphorylation of ERK and/or its substrate RSK, as well as a right-shift in proliferation dose-response curves (FIG. 2B, C and FIG. 6A, B). 1D-EiR cells had a higher level of phospho-ERK compared to their parental cells (FIG. 2A). Considering that SCH984 preferentially targets unphosphorylated ERK22, these data suggest that increased $BRAF^{V600E}$ expression attenuates the potency of inhibition by increasing the proportion of ERK in a phosphorylated state, which has a low affinity for the drug (FIG. 2D).

To determine if BRAF amplification alone is sufficient in conferring resistance, we utilized $BRAF^{V600E}$-melanoma cells (A375) engineered to express $BRAF^{V600E}$ under a doxycycline (dox)-inducible promoter[23]. Inducing $BRAF^{V600E}$ expression diminished the inhibition of pERK and pRSK, immediately after ERKi treatment (FIG. 2E) and after longer treatment intervals (FIG. 7C-E). The expression of two ERK-dependent signaling markers[24], CyclinD1 and Spry2, was restored to near baseline levels (FIG. 2F) after 48h of ERKi treatment in dox-induced cells. Due to these direct and adaptive changes, increased $BRAF^{V600E}$ expression attenuated the antiproliferative effect of ERKi-treatment in a dose-dependent and reversible manner (FIG. 2G).

We hypothesized that the fitness advantage conferred by increased $BRAF^{V600E}$ expression differs between ERK signaling inhibitors and measured the effect of $BRAF^{V600E}$ expression on RAFi-, MEKi- or ERKi-treatment (FIG. 3A and FIG. 6F-H). These experiments revealed a graded attenuation of signaling inhibition by these drugs, which correlated with the relative fitness conferred by this alteration, i.e. continued proliferation in the presence of each drug. The level of $BRAF^{V600E}$ expression required to bypass RAFi- or MEKi-treatment, i.e. fitness threshold, was lower compared to that of ERKi-treatment. Thus, a higher magnitude of amplification is required to overcome the selective pressure of directly inhibiting ERK. As a consequence, sequential exposure to ERK signaling inhibitors may serve as a selective gradient for the propagation of tumor subpopulations with a progressively higher BRAF CN and protein expression. This is in agreement with clinical observations where sequential therapy with RAF and then MEK inhibitors is ineffective in melanoma[25] or lung cancer (unpublished data) patients.

Co-targeting upstream kinases together with ERK might impose a higher fitness threshold (by diminishing the proportion of ERK in a phosphorylated state), and prevent the propagation of cells with high $BRAF^{V600E}$ expression. Indeed, combined RAFi, MEKi and ERKi-treatment durably inhibited signaling and proliferation in A375 cells induced to express intermediate- or high-level BRAFV600E (FIG. 3B, C and FIG. 7A). By comparison, almost all single agent and combination treatments achieved this effect in the absence of induction. A similar effect was observed in PDX1D- and 1D-EiR-derived cells (FIG. 7B). In agreement with these results, the three-drug combination produced the strongest antitumor effect against PDX1D and PDX1E, which was most apparent after drug withdrawal (FIG. 3D and FIG. 7C).

RAF inhibitor withdrawal confers a fitness deficit and forestalls resistance in vivo[19,26]. With this in mind, and in order to reduce the toxicity associated with maximal inhibition of ERK (FIG. 7D and E), we evaluated intermittent drug administration schemes (FIG. 4A). Concurrent administration of the three drugs for 2/4-weeks or 4/7-days had a similar antitumor effect as the continuous schedule (FIG. 4B). Regimens where the drugs were not given concurrently were less effective. The daily regimen was further optimized to maximally inhibit tumor growth without measurable toxicity in mice (FIG. 4C: 3/7-days and FIG. 8A).

The effect of this intermittent regimen was tested in 13 lung cancer and melanoma PDX models. These had several genetic alterations (FIG. 4D) and varying levels of BRAF expression (FIG. 3A —inset and FIG. 4E). The treatment produced statistically significant tumor growth inhibition in 11/11 BRAFV600-mutant PDX, with regressions in 8/11 models (FIG. 4F FIG. 8B-J). It inhibited growth in models with de-novo (PDX21), or acquired (PDX1D-EiR and PDX7-EiR), resistance to ERKi-treatment (FIG. 4B, C). In contrast, this regimen had minimal antitumor effects in BRAFWT PDX (FIG. 8D, E).

$BRAF^{V600E}$ amplification is emerging as one of the most frequent causes of acquired resistance in patients treated with RAF and/or MEK inhibitors[19-21,27]. While it was initially expected that BRAF amplified tumors would respond to ERK inhibitors, our work shows that this depends on the magnitude of amplification. Tumors or subpopulations with high-level amplification also withstand the pressure of direct ERK inhibitors, because increased $BRAF^{V600E}$ expression enhances the proportion of ERK in a phosphorylated state, which has a lower affinity for the drug. This mechanism of resistance differs from that observed with RAF or MEK inhibitors[23,28-30], and suggests that ERK inhibitors targeting phosphorylated ERK are more effective against BRAF-amplified tumors.

While increased $BRAF^{V600E}$ expression, driven by extrachromosomal DNA replication in vivo or inducible expression in vitro, enabled tumor cells to surpass the fitness threshold imposed by RAFi, MEKi or ERKi monotherapy, even cells with high levels of $BRAF^{V600E}$ expression were inhibited by a combination of these three drugs. The combination inhibited tumor growth in the presence of genetic alterations that have been associated with insensitivity to RAFi and/or MEKi[31-36], including NF1, PTEN, IRS, EGFR and TSC2. Thus, the selective pressure enacted by complete inhibition of the pathway creates a non-permissive environment for the propagation of diverse resistance-causing alterations. This effect may be even more pronounced with novel RAF inhibitors that target dimer-dependent RAF signaling[23,37]. Finally, our study describes an intermittent administration schedule that sustains the antitumor potency of this combinatorial therapy, while minimizing its toxicity in preclinical models. As it selectively inhibited $BRAF^{V600E}$-mutant PDX, while sparing those with BRAFWT, this approach may have a broad therapeutic window and merits clinical testing in patients with $BRAF^{V600}$-mutant cancer.

Methods

Cell Culture and Reagents

All cell lines used in this study were maintained in DMEM medium supplemented with 10% FBS, penicillin, streptomycin and L-glutamine. A375 cells were obtained from ATCC. A375 dox BRAF V600E were validated by the presence of fluorescence and/or BRAF expression upon dox treatment. The cell lines tested negative for mycoplasma. The inhibitors used in this study, including vemurafenib, dabrafenib, trametinib, SCH984 (aka. MK8353, Phase I) and VTx11e (aka. BDV523, Phase I) were obtained from Selleckem. Antibodies detecting BRAF (sc-5284), CyclinD1 (sc-718), Spry2 (sc-1860) or GAPDH (sc-32233) were obtained from Santa Cruz Biotechnology. Those detecting pMEK (9121), pERK (9107), ERK (9102), pRSK T359 (8753) or pRSK 5380 (12032) were obtained from Cell Signaling Technology.

Patient Derived Xenograft Models

These were established as described[38,39], in accordance with the Memorial Sloan Kettering Cancer Center Institutional Review Board. Informed consent was obtained in all cases. All animal studies were done in accordance with protocols approved by the MSKCC Animal Care and Use Committee. Melanoma models were generated previously[40]. Patient derived tissue (biopsy or surgical resection) or pleural fluid was used to establish the lung cancer models in Table I. For biopsy or resection specimens, the tumor sample was minced under aseptic conditions, vigorously washed in 1×PBS, passed through a 60-μm filter, centrifuged, and then re-suspended in 500 μL of Matrigel (BD Biosciences) at 4° C. For pleural effusions, the fluid was centrifuged in order to isolate the cellular fraction and washed several times in cold PBS. Cells were then injected subcutaneously in the flanks of NSG mice and monitored for tumor growth. When the tumors reached 1 cm in diameter, the mouse was sacrificed and the tumor divided into sections for snap freezing, frozen tissue or serial passage.

Establishment of Cell Lines from PDX Tumors

PDX were dissociated using a gentleMACS automated dissociator and human tumor dissociation kit (Miltenyi, San Diego, Calif., USA) as described[39]. Single-cell suspensions were filtered through a 70-μm mesh, washed twice with wash buffer (phosphate-buffered saline, 2% fetal bovine serum and 1 mM EDTA) and red blood cells were lysed with ACK buffer (Crystalgen Inc., Commack, N.Y., USA). Approximately 1×106 viable cells were seeded in 10 ml of DMEM supplemented with 10% FBS, L-glutamate and antibiotics. Alternatively, tumors were manually dissected and minced to a near single cell suspension and cultured as above. DNA sequencing was used to confirm that the genotype of the cultured cells matched that of PDX tumors.

Targeted Exome Sequencing

DNA derived from patients or PDX frozen tissue was subjected to targeted capture massively parallel sequencing using the Memorial Sloan Kettering-Integrated Mutation Profiling of Actionable Cancer Targets (MSK-IMPACT) sequencing assay, as previously described41. The assay comprises all coding regions of 440 key cancer-associated genes and intronic and regulatory regions of selected genes. This assay involves hybridization of barcoded libraries to custom oligonucleotides (Nimblegen SeqCap) designed to capture all protein-coding exons and select introns of 440 commonly implicated oncogenes, tumor suppressor genes, and members of pathways deemed actionable by targeted therapies. Barcoded sequence libraries were prepared using 100-250 ng genomic DNA (Kapa Biosystems) and combined into equimolar pools of 13-21 samples. The captured pools were subsequently sequenced on an Illumina HiSeq 2000 as paired-end 100-base pair reads, producing a median of 588-fold coverage per tumor. Sequence data were demultiplexed using CASAVA, and reads were aligned to the reference human genome (hg19) using BWA and post-processed using the Genome Analysis Toolkit (GATK) according to GATK best practices. MuTect and GATK were used to call single-nucleotide variants and small indels, respectively. Candidate mutations were manually reviewed using the Integrative Genomics Viewer (IGV) to eliminate likely false positive calls. Because matched normal DNA was not available, tumors were compared to a pool of 10 unmatched normal samples to eliminate common polymorphisms and systematic sequencing artifacts.

Single Cell Sequencing

Nuclei preparation from tumor samples and whole-genome amplification. Frozen tumor specimens were processed as previously described[15,16]. Briefly, tumors were minced using a single edge razor blade in 400 μl NST buffer (146 mM NaCl, 10 mM Tris base at pH 7.8, 1 mM CaCl2, 21 mM MgCl2, 0.05% BSA, 0.2% Nonidet P-40) supplemented with 4'6-diamidino-2-phenylindole (DAPI; 10 μg/mL), 0.1% DNase-free RNase A (LifeTechnologies) and incubated on wet ice for 1 h. Nuclei suspension were washed twice with NST-DAPI (800 μl wash, 7 minutes at 5000 rpm centrifugation), then filtered twice through a strainer mesh (35 μm) and collected into a 5 ml Polystyrene round-bottom tube. Samples were rested on wet ice for immediate sorting or frozen in dry ice for transportation or supplemented with 10% DMSO and placed in a freezing container to obtain a ~1° C./min cooling rate for nuclear integrity cryopreservation of nuclei overnight at −80° C. Single nuclei were sorted by FACS using the BD Biosystems Aria II flow cytometer by gating cellular distributions with differences in their total genomic DNA content according to DAPI intensity. First, a small amount of prepared nuclei from each tumour sample was mixed with a diploid control sample (derived from a lymphoblastoid cell line of a healthy individual, 315A) to accurately determine the diploid peak position within the tumour and establish FACS collection gates. Before sorting single nuclei, a few thousand cells were sorted to determine the DNA content distributions for gating. Visual inspection of the nuclei using DAPI staining was performed to ensure the integrity of the nuclei sorted. Single nuclei were deposited into individual wells in the 96-well plate containing 9 μl of lysis solution in each well from the Sigma-Aldrich GenomePlex WGA4 kit. Whole-genome amplification was performed on single flow-sorted nuclei as described in the Sigma-Aldrich GenomePlex WGA4 kit protocol. WGAs were assessed on a 1.5% agarose gel to confirm amplification. The WGA products were then cleaned using QIAamp DNA Mini Kit (Qiagen), eluted in 50 μl EB buffer.

Library preparation and sequencing. Eight hundred nanograms (800 ng) of WGA products were diluted to 75 μL in EB buffer (Qiagen) and acoustically sonicated using the Covaris E210 focus acoustics system with a target base pair peak of 300 (i.e. Duty Cycle: 10%, Intensity: 4, Cycle per Bust: 200 and Time: 80 sec). The sonicated WGA was end repaired using NEBNext End Repair module following manufacturer's protocol (New England Biolabs). The end-repaired DNA was cleaned with QIAamp DNA Mini Kit (Qiagen), eluted in 42 μL EB buffer and subjected to dA-Tailing suing the NEBNext dA-Tailing following manufacturer's protocol (New England Biolabs). Then, the dA-tailed DNA was cleaned with QIAamp DNA Mini Kit (Qiagen), eluted in 35 WEB buffer, and exactly 34 μL of eluate was combined with 10 μL of 2× Quick Ligation Reaction Buffer, 4 μL of 10 μM barcoded adapter (in-lane and TruSeq Dual-Index adapters sequences are listed in Supplementary Table 4) and 2 μL Quick T4 DNA Ligase (New England Biolabs), and incubated at 20° C. for 15 min. The ligated product was then combined with 26.25 μL Agencourt AMPure XP magnetic beads (Beckman Coulter) (ligated product/magnetic bead ratio 0.35), thoroughly mixed and incubated at RT for 10'. The magnetic beads-DNA complexes were washed twice with freshly prepared 80% ethanol, dried for 10 min at RT and finally eluted in 30 μL of EB buffer and quantified using a Qubit Fluorometer. The indexed/barcoded libraries were then pooled mixing equal amounts (~20 ng each), quantitated and PCR-enriched using NEBNext High-Fidelity 2×PCR Master Mix (in duplicate) containing up to 80 ng of pooled library and 2.5 μL of enrichment primers. The reactions were incubated 30 sec at 98° C. and then 5 cycles of 10 sec at 98° C., 30 sec at 60/65° C. (depending on primer set) and 30 sec at 72° C., with a final 5 min incubation at 72° C. to ensure polished ends. Individual replicates were then combined, cleaned using the QIAamp DNA Mini Kit (Qiagen) and eluted in 50 μL EB buffer. Enriched libraries were assessed on a Bioanalyzer instrument (Agilent Technologies), quantified and sequenced on a HiSeq4000 instrument (PE 2×150 bp).

CN analysis of single cells. Multiplexed single-cell sequencing libraries were split according to their unique barcode identifiers specified by the first seven bases of the sequencing reads. Single-cell sequencing data were aligned to the human reference genome hg19 (or to the mouse genome mm10 in case of the stromal cells) using Bowtie[42]. Sequencing reads were sorted, followed by removal of PCR duplicates, and then indexed using SAMtools[43]. CN assessment of single cells was performed using the Ginkgo5 pipeline[44] (qb.cshl.edu/ginkgo), using the following settings: variable bin size of 250 kb, bins based on simulations of 101 bp, CBS segmentation. Bad bins and Y-chr pseudo-autosomal regions were masked and the clustering was done using Ward's distance and Manhattan distance algorithms on integer copy number values.

Fluorescence In Situ Hybridization

FISH analysis was performed on formalin fixed paraffin embedded (FFPE) sections or cell line suspension, as described.[45] Cell lines were harvested and fixed in methanol: acetic acid (3:1) as per standard procedures. FISH analysis was performed using a 2-color BRAF/Cen7 Probe. The probe mix consisted of BAC clones containing the full length BRAF gene (clones RP11-788O6, RP11-1065D4, and RP11-133N19; labeled with Red dUTP) and a centromeric repeat plasmid for chromosome 7 served as the control (clone p7t1; labeled with Green dUTP). Probe labeling, tissue processing, hybridization, post-hybridization washing, and fluorescence detection were performed according to standard laboratory procedures. Slides were scanned using a Zeiss Axioplan 2i epifluorescence microscope equipped with a megapixel CCD camera (CV-M4+CL, JAI) controlled by Isis 5.5.9 imaging software (MetaSystems Group Inc, Waltham, Mass.). The entire hybridized area or tissue section was first scanned through 63× objective, intra-tumoral heterogeneity assessed, and representative regions imaged (compressed/merged stack of 12 z-section images taken at 0.5 micron intervals for paraffin sections). For each sample, a minimum of 100 discrete nuclei and 20 metaphases (two cell lines) were analyzed. Amplification was defined as BRAF:Cen7 (control) ratio of ≥2.0, >10 copies of BRAF (independent of control locus) or at least one small cluster of BRAF (≥4 signals resulting from tandem repeat/duplication). In cells with high-level amplification, signals ≥20 could not be accurately counted and therefore given a score of 20. Cells with 3~5 and 6~10 discrete copies of BRAF/Cen7 were considered to be polysomic and high-polysomic respectively.

Mass Spectrometry Detection of BRAF Protein Expression In Vivo

BRAF (Total or V600E) protein was quantitated by SRM-MS as previously described[46]. Briefly, tissue sections (10 μM) from FFPE blocks were placed onto DIRECTOR® microdissection slides followed by deparaffinization and hematoxylin staining. Tumor areas were marked by a board-certified pathologist and a 12 mm2 section containing nearly 50,000 malignant cells was microdissected and solubilized to tryptic peptides using Liquid Tissue® technology. The solution was subjected to SRM-MS analysis using stable isotope-labeled internal standard peptides for BRAFV600E and total BRAF quantitation. Actin and tubulin quantitation was monitored to verify sample quality and efficiency of microdissection. On-column injection resulted in 5 fmol of isotopically labeled internal standard peptides and 1 μg (~4000 cells) of total tumor protein as measured by microBCA (ThermoFisher Scientific, San Jose, Calif.). Instrumental analyses were performed on TSQ Quantiva triple quadrupole mass spectrometer (Thermo Scientific, San Jose, Calif.), as previously described[47].

Viability Assays

Cells were grown in the presence or absence of inhibitor for various times. Viable cells were determined by using the CellTiter Glo (Promega) assay as described previously[48].

Animal Studies

Nu/nu athymic or NSG mice were obtained from the Harlan Laboratories and maintained in compliance with IACUC guidelines. Animals implanted with xenografts were chosen for efficacy studies in an unbiased manner. In rare instances animals were excluded if the subcutaneous tumors failed to engraft. Tumor bearing animals were treated in a random fashion with drug or the appropriate vehicle control. Subcutaneous xenografts and tumor measurements were performed as described[11] in a non-blinded manner by a research technician not involved in the rest of the study. The data were plotted in Prism and reported as tumor volume over time. For 5 mice per cohort, the power to detect an odds parameter of 14.0 for each pairwise comparison, with two-sided α level of 0.05, was 80%. Doubling times were calculated by fitting tumor volumes into exponential growth curves and determining their rate constants in Prism. Negative doubling times indicate tumor regression compared to the pre-treatment size. Statistically significant differences in rate constants were determined by using the extra-sum-of-squares F test (with $p<0.05$) embedded in Prism. Animal weights were used as a marker of toxicity, and reported either as absolute values or as % change relative to the weight of the animal prior to treatment onset. When toxicity was severe to cause animal death, a weight of zero was assigned in order to facilitate calculations. Unless otherwise stated, groups were compared using non-parametric permutation tests. All animal studies were performed in compliance with institutional guidelines under an IACUC approved protocol (Memorial Sloan-Kettering Cancer Center No. 09-05-009).

Example 2

Treatment of BRAF$^{V600E}$-Mutant Tumors in Human Clinical Trials

A phase I/II clinical trial of RAF/MEK/ERK-inhibitor triple therapy in BRAF$^{V600E}$-mutant cancer (such as melanoma or lung adenocarcinoma) is performed as follows.

Any of the RAF inhibitors, MEK inhibitors, and ERK inhibitors described in this patent specification can be used. One of each is selected. The starting dosage for each agent is the recommended maximum tolerated dose for each agent, as determined in their respective phase I trials. For drugs for which a phase I trial has not yet been performed, the maximum tolerated dose is determined in dose escalation cohorts. An intermittent dosing schedule of the type described elsewhere herein is employed. One of the dosing schedules identified in Example 1 as being both effective and having reduced toxicity in mouse PDX models is used as a starting point. In order to account for any differences between the effects in mice and humans, additional cohorts are included in the clinical trial to test variations of the intermittent dosing schedule. In each cohort the human subjects are treated with the three active agents concurrently for 1, 2, 3, or 4 days. This is the "treatment on" time. This is followed by a "treatment off" time of 6, 5, 4, or 3 days, respectively for each cohort. That is for the first cohort the "treatment on" time is 1 day and the "treatment off" time is 6 days. For the second cohort the "treatment on" time is 2 days and the "treatment off" time is 5 days. For the third cohort the "treatment on" time is 3 days and the "treatment off" time is 4 days. For the fourth cohort the "treatment on" time is 4 days and the "treatment off" time is 3 days. The "treatment on" and "treatment off" cycles are repeated for the duration of the entire treatment period.

In the event that toxicity is observed, the dosing schedule is adjusted to prolong the "treatment off" time, for example by employing an additional week of "treatment off" time. Thus, the first cohort is modified to have a "treatment on" time of 1 day and a "treatment off" time of 13 days. The second cohort is modified to have a "treatment on" time of 2 days and a "treatment off" time of 12 days. The third cohort is modified to have a "treatment on" time of 3 days and a "treatment off" time of 11 days. The fourth cohort is modified to have a "treatment on" time is 4 days and a "treatment off" time of 10 days.

The patient cohorts having with the best tolerated regimens are expanded to include additional human subjects, in order to more thoroughly test the effectiveness of that regimen.

Additional cohorts can be tested depending on the outcome observed in the above cohorts. Such cohorts may have further adjustments to the "treatment on" and "treatment off" times, and/or may have adjustments to the dosages of the individual active agents used, for example to reduce the dose of one or more of the three active agents to about 90% of the maximum tolerated dose, or about 80% of the maximum tolerated dose, or about 70% of the maximum tolerated dose, or about 60% of the maximum tolerated dose, or about 50% of the maximum tolerated dose.

REFERENCE LIST

1. Chapman, P. B. et al. Improved survival with vemurafenib in melanoma with BRAF$^{V600E}$ mutation. The New England journal of medicine 364, 2507-2516, doi:10.1056/NEJMoa1103782 (2011).
2. Flaherty, K. T. et al. Inhibition of mutated, activated BRAF in metastatic melanoma. The New England journal of medicine 363, 809-819, doi:10.1056/NEJMoa1002011 (2010).
3. Planchard, D. et al. Dabrafenib in patients with BRAF($^{B600E}$)-positive advanced non-small-cell lung cancer: a single-arm, multicentre, open-label, phase 2 trial. The Lancet. Oncology 17, 642-650, doi:10.1016/S1470-2045 (16)00077-2 (2016).
4. Hyman, D. M. et al. Vemurafenib in Multiple Nonmelanoma Cancers with BRAF V600 Mutations. The New England journal of medicine 373, 726-736, doi:10.1056/NEJMoa1502309 (2015).
5. Flaherty, K. T. et al. Combined BRAF and MEK inhibition in melanoma with BRAF V600 mutations. The New England journal of medicine 367, 1694-1703, doi: 10.1056/NEJMoa1210093 (2012).
6. Larkin, J. et al. Combined vemurafenib and cobimetinib in BRAF-mutated melanoma. The New England journal of medicine 371, 1867-1876, doi:10.1056/NEJMoa1408868 (2014).
7. Long, G. V. et al. Combined BRAF and MEK inhibition versus BRAF inhibition alone in melanoma. The New England journal of medicine 371, 1877-1888, doi: 10.1056/NEJMoa1406037 (2014).
8. Robert, C. et al. Improved overall survival in melanoma with combined dabrafenib and trametinib. The New England journal of medicine 372, 30-39, doi:10.1056/NEJMoa1412690 (2015).
9. Planchard, D. et al. Dabrafenib plus trametinib in patients with previously treated BRAF($^{V600E}$)-mutant metastatic non-small cell lung cancer: an open-label, multicentre phase 2 trial. The Lancet. Oncology 17, 984-993, doi: 10.1016/S1470-2045(16)30146-2 (2016).
10. Bollag, G. et al. Clinical efficacy of a RAF inhibitor needs broad target blockade in BRAF-mutant melanoma. Nature 467, 596-599, doi:10.1038/nature09454 (2010).
11. Lito, P. et al. Relief of profound feedback inhibition of mitogenic signaling by RAF inhibitors attenuates their activity in BRAF$^{V600E}$ melanomas. Cancer cell 22, 668-682, doi:10.1016/j.ccr.2012.10.009 (2012).
12. Cancer Genome Atlas Research, N. Comprehensive molecular profiling of lung adenocarcinoma. Nature 511, 543-550, doi:10.1038/nature13385 (2014).
13. Morris, E. J. et al. Discovery of a novel ERK inhibitor with activity in models of acquired resistance to BRAF and MEK inhibitors. Cancer discovery 3, 742-750, doi: 10.1158/2159-8290.CD-13-0070 (2013).
14. Wong, D. J. et al. Antitumor activity of the ERK inhibitor SCH772984 [corrected] against BRAF mutant, NRAS mutant and wild-type melanoma. Molecular cancer 13, 194, doi:10.1186/1476-4598-13-194 (2014).
15. Baslan, T. et al. Genome-wide copy number analysis of single cells. Nature protocols 7, 1024-1041, doi:10.1038/nprot.2012.039 (2012).
16. Navin, N. et al. Tumour evolution inferred by single-cell sequencing. Nature 472, 90-94, doi:10.1038/nature09807 (2011).
17. Baslan, T. et al. Optimizing sparse sequencing of single cells for highly multiplex copy number profiling. Genome research 25, 714-724, doi:10.1101/gr.188060.114 (2015).
18. Weir, B. A. et al. Characterizing the cancer genome in lung adenocarcinoma. Nature 450, 893-898, doi:10.1038/nature06358 (2007).
19. Das Thakur, M. et al. Modelling vemurafenib resistance in melanoma reveals a strategy to forestall drug resistance. Nature 494, 251-255, doi:10.1038/nature11814 (2013).
20. Shi, H. et al. Acquired resistance and clonal evolution in melanoma during BRAF inhibitor therapy. Cancer discovery 4, 80-93, doi:10.1158/2159-8290.CD-13-0642 (2014).
21. Shi, H. et al. Melanoma whole-exome sequencing identifies ($^{V600E}$)B-RAF amplification-mediated acquired B-RAF inhibitor resistance. Nature communications 3, 724, doi:10.1038/ncomms1727 (2012).
22. Jha, S. et al. Dissecting Therapeutic Resistance to ERK Inhibition. Molecular cancer therapeutics 15, 548-559, doi:10.1158/1535-7163.MCT-15-0172 (2016).
23. Yao, Z. et al. BRAF Mutants Evade ERK-Dependent Feedback by Different Mechanisms that Determine Their Sensitivity to Pharmacologic Inhibition. Cancer cell 28, 370-383, doi:10.1016/j.ccell.2015.08.001 (2015).

24. Joseph, E. W. et al. The RAF inhibitor PLX4032 inhibits ERK signaling and tumor cell proliferation in a $^{V600E}$ BRAF-selective manner. Proceedings of the National Academy of Sciences of the United States of America 107, 14903-14908, doi:10.1073/pnas.1008990107 (2010).
25. Kim, K. B. et al. Phase II study of the MEK1/MEK2 inhibitor Trametinib in patients with metastatic BRAF-mutant cutaneous melanoma previously treated with or without a BRAF inhibitor. Journal of clinical oncology: official journal of the American Society of Clinical Oncology 31, 482-489, doi:10.1200/JCO.2012.43.5966 (2013).
26. Holderfield, M., Deuker, M. M., McCormick, F. & McMahon, M. Targeting RAF kinases for cancer therapy: BRAF-mutated melanoma and beyond. Nature reviews. Cancer 14, 455-467, doi:10.1038/nrc3760 (2014).
27. Lito, P., Rosen, N. & Solit, D. B. Tumor adaptation and resistance to RAF inhibitors. Nature medicine 19, 1401-1409, doi:10.1038/nm.3392 (2013).
28. Heidorn, S. J. et al. Kinase-dead BRAF and oncogenic RAS cooperate to drive tumor progression through CRAF. Cell 140, 209-221, doi:10.1016/j.cell.2009.12.040 (2010).
29. Poulikakos, P. I., Zhang, C., Bollag, G., Shokat, K. M. & Rosen, N. RAF inhibitors transactivate RAF dimers and ERK signalling in cells with wild-type BRAF. Nature 464, 427-430, doi:10.1038/nature08902 (2010).
30. Lito, P. et al. Disruption of CRAF-mediated MEK activation is required for effective MEK inhibition in KRAS mutant tumors. Cancer cell 25, 697-710, doi:10.1016/j.ccr.2014.03.011 (2014).
31. Corcoran, R. B. et al. EGFR-mediated re-activation of MAPK signaling contributes to insensitivity of BRAF mutant colorectal cancers to RAF inhibition with vemurafenib. Cancer discovery 2, 227-235, doi:10.1158/2159-8290.CD-11-0341 (2012).
32. Prahallad, A. et al. Unresponsiveness of colon cancer to BRAF$^{(V600E)}$ inhibition through feedback activation of EGFR. Nature 483, 100-103, doi:10.1038/nature10868 (2012).
33. Shi, H. et al. A novel AKT1 mutant amplifies an adaptive melanoma response to BRAF inhibition. Cancer discovery 4, 69-79, doi:10.1158/2159-8290.CD-13-0279 (2014).
34. Sun, C. et al. Reversible and adaptive resistance to BRAF$^{(V600E)}$ inhibition in melanoma. Nature 508, 118-122, doi:10.1038/nature13121 (2014).
35. Maertens, O. et al. Elucidating distinct roles for NF1 in melanomagenesis. Cancer discovery 3, 338-349, doi: 10.1158/2159-8290.CD-12-0313 (2013).
36. Johannessen, C. M. et al. A melanocyte lineage program confers resistance to MAP kinase pathway inhibition. Nature 504, 138-142, doi:10.1038/nature12688 (2013).
37. Zhang, C. et al. RAF inhibitors that evade paradoxical MAPK pathway activation. Nature 526, 583-586, doi: 10.1038/nature14982 (2015).
38. Nguyen, A. et al. PKLR promotes colorectal cancer liver colonization through induction of glutathione synthesis. The Journal of clinical investigation 126, 681-694, doi: 10.1172/JCI83587 (2016).
39. Poirier, J. T. et al. DNA methylation in small cell lung cancer defines distinct disease subtypes and correlates with high expression of EZH2. Oncogene 34, 5869-5878, doi:10.1038/onc.2015.38 (2015).
40. Einarsdottir, B. O. et al. Melanoma patient-derived xenografts accurately model the disease and develop fast enough to guide treatment decisions. Oncotarget 5, 9609-9618, doi:10.18632/oncotarget.2445 (2014).
41. Cheng, D. T. et al. Memorial Sloan Kettering-Integrated Mutation Profiling of Actionable Cancer Targets (MSK-IMPACT): A Hybridization Capture-Based Next-Generation Sequencing Clinical Assay for Solid Tumor Molecular Oncology. The Journal of molecular diagnostics: JMD 17, 251-264, doi:10.1016/j.jmoldx.2014.12.006 (2015).
42. Langmead, B., Trapnell, C., Pop, M. & Salzberg, S. L. Ultrafast and memory-efficient alignment of short DNA sequences to the human genome. Genome biology 10, R25, doi:10.1186/gb-2009-10-3-r25 (2009).
43. Li, H. & Durbin, R. Fast and accurate short read alignment with Burrows-Wheeler transform. Bioinformatics 25, 1754-1760, doi:10.1093/bioinformatics/btp324 (2009).
44. Garvin, T. et al. Interactive analysis and assessment of single-cell copy-number variations. Nature methods 12, 1058-1060, doi:10.1038/nmeth.3578 (2015).
45. Wanjala, J. et al. Identifying actionable targets through integrative analyses of GEM model and human prostate cancer genomic profiling. Molecular cancer therapeutics 14, 278-288, doi:10.1158/1535-7163.MCT-14-0542-T (2015).
46. Hembrough, T. et al. Application of selected reaction monitoring for multiplex quantification of clinically validated biomarkers in formalin-fixed, paraffin-embedded tumor tissue. The Journal of molecular diagnostics: JMD 15, 454-465, doi:10.1016/j.jmoldx.2013.03.002 (2013).
47. Catenacci, D. V. et al. Absolute quantitation of Met using mass spectrometry for clinical application: assay precision, stability, and correlation with MET gene amplification in FFPE tumor tissue. PloS one 9, e100586, doi: 10.1371/journal.pone.0100586 (2014).
48. Lito, P., Solomon, M., Li, L. S., Hansen, R. & Rosen, N. Allele-specific inhibitors inactivate mutant KRAS G12C by a trapping mechanism. Science 351, 604-608, doi: 10.1126/science.aad6204 (2016).

I claim:

1. A method of treating a BRAF$^{V600E}$ mutant lung tumor or melanoma in a subject in need thereof, the method comprising concurrently administering an effective amount of: (a) a RAF inhibitor, (b) a MEK inhibitor, and (c) an ERK inhibitor to a subject having a BRAF$^{V600E}$ mutant lung tumor or melanoma on an intermittent dosing schedule, thereby treating the lung tumor or melanoma in the subject.

2. The method of claim 1, wherein the RAF inhibitor is selected from the group consisting of Dabrafenib (GSK2118436), Dabrafenib Mesylate (GSK-2118436 Mesylate), Encorafenib (LGX818), Vemurafenib (PLX4032, RG7204), Sorafenib, Sorafenib Tosylate, Zelboraf, Tafinlar, AZ 628, B-Raf IN 1, CEP-32496, CEP-32496 hydrochloride, GDC-0879, GW 5074, HG6-64-1, L-779450, LGX818, LY3009120, MLN 2480 (BIM-024), PLX 4720, PLX7904, PLX8394, Sorafenib, Sorafenib Tosylate, R05126766 (CH5126766), RAF265 (CHIR-265), TAK-632, ZM 336372, SB590885, GW5074, and Raf265 derivative.

3. The method of claim 1, wherein the MEK inhibitor is selected from the group consisting of Trametinib (Mekinist, GSK1120212), Cobimetinib (GDC-0973, RG7420), Selumetinib (AZD6244), Binimetinib (MEK162, ARRY-162, ARRY-438162), Pimasertib (AS-703026), Refametinib (RDEA119, Bay 86-9766), PD0325901, U0126-EtOH I, PD184352 (CI-1040), PD98059, BIX02189, GDC-0623, BI-847325, SL327, BIX02188, AZD8330, TAK-733, Honokiol, and PD318088.

4. The method of claim 1, wherein the ERK inhibitor inhibits un-phosphorylated ERK.

5. The method of claim 1, wherein the ERK inhibitor inhibits phosphorylated ERK.

6. The method of claim 1, wherein the ERK inhibitor is selected from the group consisting of SCH984 (MK8353), Ulixertinib (BVD-523, VRT752271, VTx11e), SCH772984, ERK5-IN-1, XMD8-92, FR 180204, DEL-22379, GDC-0994, and VX-11e.

7. The method of claim 1, wherein the subject has a BRAF mutant tumor that is resistant to treatment using only a RAF inhibitor and a MEK inhibitor.

8. The method of claim 1, wherein the RAF inhibitor, the MEK inhibitor, and/or the ERK inhibitor are administered systemically.

9. The method of claim 1, wherein the RAF inhibitor, the MEK inhibitor, and/or the ERK inhibitor are administered locally.

10. The method of claim 1, wherein the RAF inhibitor, the MEK inhibitor, and the ERK inhibitor are administered on only 3 out of every 7 days.

11. The method of claim 10, wherein the 3 days are 3 consecutive days.

12. The method of claim 1, wherein the RAF inhibitor, the MEK inhibitor, and the ERK inhibitor are administered on only 4 out of every 7 days.

13. The method of claim 12, wherein the 4 days are 4 consecutive days.

14. The method of claim 1, wherein the RAF inhibitor, the MEK inhibitor, and the ERK inhibitor are administered for only 1 out of every 2 weeks.

15. The method of claim 1, wherein the intermittent dosing schedule comprises:
   (i) administering the RAF inhibitor, the MEK inhibitor, and the ERK inhibitor daily for 3 consecutive days,
   (ii) not administering the RAF inhibitor, the MEK inhibitor, and the ERK inhibitor daily for a period of 4 consecutive days immediately following step (i), and
   (iii) subsequently repeating steps (i) and (ii) one or more times.

16. The method of claim 1, wherein the intermittent dosing schedule comprises:
   (i) administering the RAF inhibitor, the MEK inhibitor, and the ERK inhibitor daily for 4 consecutive days, followed by
   (ii) a period of 3 consecutive days during which the RAF inhibitor, the MEK inhibitor, and the ERK inhibitor are not administered, and
   (iii) subsequently repeating steps (i) and (ii) one or more times.

17. The method of claim 1, wherein the intermittent dosing schedule comprises:
   (i) administering the RAF inhibitor, the MEK inhibitor, and the ERK inhibitor daily for 7 consecutive days, followed by
   (ii) a period of 7 consecutive days during which the RAF inhibitor, the MEK inhibitor, and the ERK inhibitor are not administered, and
   (iii) subsequently repeating steps (i) and (ii) one or more times.

18. The method of claim 1, further comprising performing a diagnostic test to determine if the subject has a tumor that comprises a $BRAF^{V600E}$ mutation, prior to administering the RAF inhibitor, MEK inhibitor, and ERK inhibitor to the subject.

* * * * *